(12) United States Patent
Maruo et al.

(10) Patent No.: US 7,364,700 B2
(45) Date of Patent: Apr. 29, 2008

(54) OZONE GAS SENSING ELEMENT, DETECTION APPARATUS, AND MEASUREMENT METHOD

(75) Inventors: Yasuko Maruo, Kanagawa (JP); Shigeo Ogawa, Kanagawa (JP); Seizou Sakata, Tokyo (JP); Tohru Tanaka, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 615 days.

(21) Appl. No.: 10/650,533

(22) Filed: Aug. 27, 2003

(65) Prior Publication Data

US 2004/0131501 A1     Jul. 8, 2004

(30) Foreign Application Priority Data

Aug. 28, 2002  (JP)  .............................. 2002-249503
Dec. 3, 2002   (JP)  .............................. 2002-351034

(51) Int. Cl.
    *G01N 33/00* (2006.01)
(52) U.S. Cl. .......................... 422/91; 436/135; 422/83; 422/86; 422/87; 422/88
(58) Field of Classification Search ................ 436/135; 422/91, 83, 86, 87, 88
    See application file for complete search history.

(56) References Cited

U.S. PATENT DOCUMENTS

| | | | |
|---|---|---|---|
| 4,859,607 A | 8/1989 | Lambert et al. | |
| 5,185,129 A | 2/1993 | Koutrakis et al. | |
| 6,164,146 A | 12/2000 | Wydeven | |
| 6,336,964 B1 | 1/2002 | Omatsu et al. | |
| 6,368,867 B1 | 4/2002 | Gibson et al. | |
| 6,911,179 B2 * | 6/2005 | Ando et al. | 422/82.02 |

FOREIGN PATENT DOCUMENTS

| | | |
|---|---|---|
| DE | 196 19 226 A1 | 11/1997 |
| JP | 62 291564 | 12/1987 |
| JP | 7-72137 | 3/1995 |
| JP | 10-115591 | 5/1998 |
| JP | 10-316910 | 12/1998 |
| JP | 02 165049 | 6/1999 |

OTHER PUBLICATIONS

"Quantitative Determination of Aqueous-Phase Ozone by Chemiluminescence Using Indigo-5,5'-disulfonate", K. Takeuchi et al., Mar. 15, 1999, vol. 61, No. 6, XP00026193.

(Continued)

*Primary Examiner*—Jill Warden
*Assistant Examiner*—Samuel P Siefke
(74) *Attorney, Agent, or Firm*—Blakely, Sokoloff, Taylor & Zafman

(57) ABSTRACT

A sensing element in which a dye that changes in the light absorption characteristic of the visible region upon reaction with ozone gas is deposited in the pores of a porous material is prepared. A change in dye before and after exposing the sensing element to a measurement environment for a predetermined time is measured. The ozone gas amount in measurement target air is measured on the basis of the change in dye.

22 Claims, 9 Drawing Sheets

OTHER PUBLICATIONS

"Flow Injection Analysis of Aqueous Ozone Based on the Ozone Decoloration Reaction of 1-(20Hydroxy-5-Sulfophenylazo)-2-Naphtol" by Yasuo Onari; No. 13 1989; pp. 30-31; Published by MIE Industrial Research Institute, abstract.

"Active Intrinsic Optical Chemical Sensor for the Detection and Measurement of Carbon Monoxide in Air" by Steven J. Syracuse, et al.; *Proceedings SPIE—The International Society for Optical Engineering*; vol. 2293; Jul. 26-27, 1994; San Diego, CA; pp. 186-197.

"Glassy spectral gas sensors based on the immobilized indicators" by Alexander F. Novikov, et al.; *roceedings SPIE—The International Society for Optical Engineering*; vol. 2550; Jul. 11-12, 1995; San Diego, CA; pp. 119-129.

Preprints of 11th Fall Meeting of The Ceramic Society of Japan; Oct. 1, 1998, abstract.

"Vycor Porous Glass (Thirsty Glass) as a Reaction Medium for Optical Waveguide Based Chemical Vapor Detectors" by Thaddeus J. Novak et al.; *Spectroscopy Letters*—An International Journal for Rapid Communication; vol. 21, No. 2, 1988; pp. 127-145.

"An $NO_2$ sensor using porous glass (2)" by Takashi Ohyama, et al.; Jun. 25, 1999; NTT Lifestyle and Environmental Technology Laboratories; pp. 49-54, abstract.

\* cited by examiner

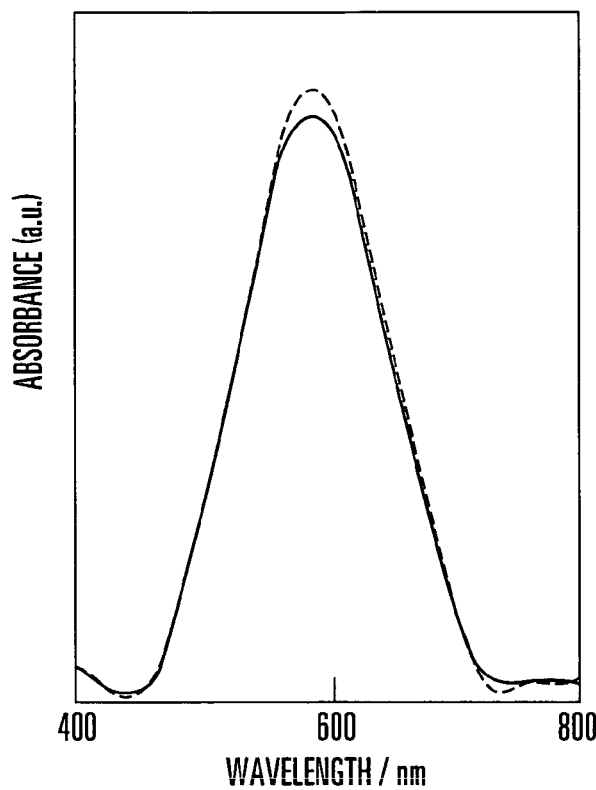
DYE : INDIGO CARMINE DISODIUM SALT
ACID : HYDROCHLORIC ACID
F I G. 11
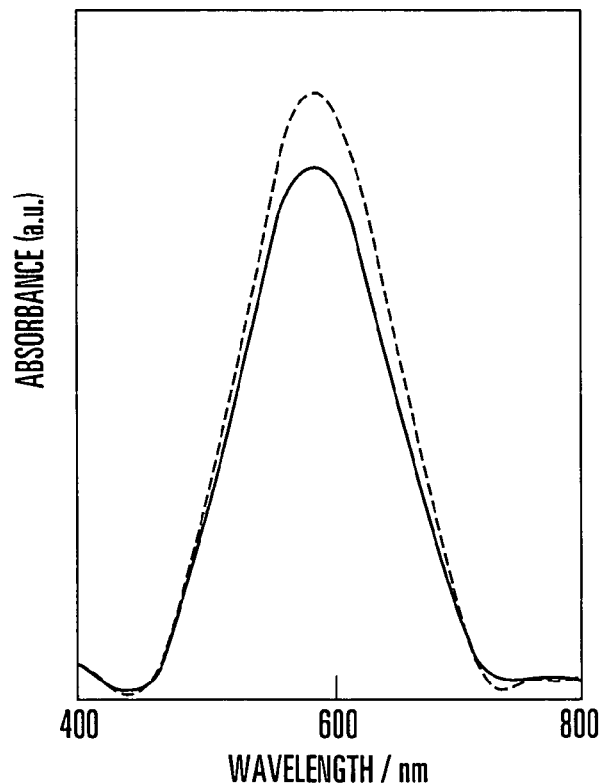
DYE : INDIGO CARMINE DISODIUM SALT
ACID GAS SORBENT : HYDROCHLORIC ACID + GLYCEROL
F I G. 12

OZONE GAS SENSING ELEMENT, DETECTION APPARATUS, AND MEASUREMENT METHOD

BACKGROUND OF THE INVENTION

The present invention relates to an ozone gas sensing element, detection apparatus, and measurement method.

At present, air pollution by $NO_x$, SPM, and photochemical oxidant occurs, and the influence on the environment is serious. Ozone as a main component of photochemical oxidant is produced by photochemical reaction of a pollutant such as $NO_x$ or hydrocarbon emitted by factories, business offices, and vehicles upon irradiation with sunlight, and causes a photochemical smog.

In Japan, air quality standards have been set for, e.g., the photochemical oxidant concentrations of these substances in air. The gas concentration is measured using analytical instruments that utilize ultraviolet absorption in general air monitoring stations at many places. The air quality standard is an average of 60 ppb or less per hour.

In gas concentration measurement using analytical instruments, a small amount of gas at several ppb can be measured. However, this instrument is expensive and requires maintenance. Analytical instrument requires very high power cost, apparatus maintenance cost, and the like. In addition, many restrictions are posed such that a power supply, a standard gas for calibration, and humidity-controlled dedicated room must be ensured.

In order to perform investigation of the gas concentration distribution and evaluation of the influence on the terrestrial environment at high precision, the number of monitoring points must be increased to monitor the environment on a nationwide scale. For this purpose, a demand has arisen for cumulative use of low-cost, compact, and easy-to-use gas sensors or passive measurement methods (or monitoring apparatuses).

To meet this demand, a semiconductor gas sensor, solid electrolyte gas sensor, electrochemical gas sensor, quartz crystal oscillation gas sensor, and the like are widely developed. However, these gas sensors are developed for evaluating a response within a short time, and not for monitoring which requires data accumulation. If accumulation is necessary, the gas sensor must always be operated. The detection limit is sub-ppm (1 ppm or less), and the gas sensor cannot cope with the detection of ozone at the concentration (e.g., about 10 ppb for ozone) in an actual environment. The influence of another gas cannot be ignored in many cases.

Also, a method using a passive sampler is developed for long-term-averaged measurement on the spot, and is not proper for cumulative use. This method suffers problems such that an operator must go to the site and an individual difference occurs in reading color. The interference or disturbance of another gas often poses a problem.

As the passive measurement method, ozone is sampled by a suction pump into a glass bottle cleaned with purified water so as not to mix air. Ozone in water is absorbed in a potassium iodide solution to titrate precipitated iodine. This method requires not only a sample, but also peripheral devices such as a pump and pH adjustment immediately after water sampling. Further, detection processing must be executed.

Conventional gas concentration measurement requires an expensive, bulky apparatus arrangement in order to detect ozone gas at high precision in ppb order in accordance with the air quality standard. Measurement is cumbersome, and ozone gas cannot be easily detected.

SUMMARY OF THE INVENTION

It is an object of the present invention to provide an ozone gas sensing element, detection apparatus (measurement apparatus), and detection method (measurement method) capable of detecting ozone gas more easily at higher precision than the prior art.

It is another object of the present invention to provide an ozone gas sensing element, detection apparatus (measurement apparatus), and detection method (measurement method) capable of cumulative use.

It is still another object of the present invention to provide an ozone gas sensing element, detection apparatus (measurement apparatus), and detection method (measurement method) in which interference or disturbance of another gas is negligible.

To achieve the above objects, an ozone gas measurement method according to the present invention comprises the steps of preparing a sensing element in which a dye (stain) that changes in a light absorption characteristic of a visible region upon reaction with ozone gas is deposited in a pore of a porous material, exposing the sensing element to a measurement environment for a predetermined time, and measuring an ozone gas amount in a target gas on the basis of a change in the light absorption before and after exposing the sensing element to the measurement environment for a predetermined time.

An ozone gas sensing element according to the present invention comprises a porous material, and a dye (stain) which is deposited in a pore of the porous material and changes in a light absorption characteristic of a visible region upon reaction with ozone gas.

An ozone gas measurement apparatus according to the present invention comprises a light-emitting unit, a light-detecting unit, a sensing element, and a signal processing unit, wherein the light-emitting unit emits light having a predetermined wavelength, the sensing element is interposed between the light-emitting unit and the light-detecting unit, and comprises a porous material, and a dye which is deposited in a pore of the porous material and changes in a light absorption characteristic of a visible region upon reaction with ozone gas, the light-detecting unit comprises a light-receiving surface arranged to face the light-emitting unit, receives, via the sensing element, light emitted by the light-emitting unit, and outputs a signal corresponding to a light quantity received by the light-receiving surface, and the signal processing unit calculates an ozone gas amount on the basis of the signal output from the light-detecting unit and a light absorption characteristic, obtained in advance, of the sensing element which contains the dye before reaction with the ozone gas.

BRIEF DESCRIPTION OF THE DRAWINGS

FIG. 11 is a graph showing the results of two absorbance measurements in an ozone gas detection method according to the fifth embodiment of the present invention;

FIG. 12 is a graph showing the results of two absorbance measurements in an ozone gas detection method according to the sixth embodiment of the present invention;

DESCRIPTION OF THE PREFERRED EMBODIMENTS

Preferred embodiments of the present invention will be described below with reference to the accompanying drawings.

First Embodiment

An ozone gas detection method (measurement method) according to the first embodiment will be explained.

A sensing element fabrication method will be described.

Figure 1A:
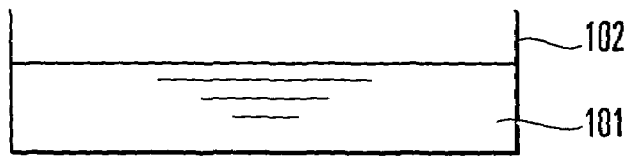
FIGS. 1A to 1C are views for explaining a method of manufacturing an ozone gas sensing element according to an embodiment of the present invention.

As shown in FIG. 1A, a mixture solution 101 containing Orange I ethanol solution and water is prepared in a vessel 102. The Orange I concentration is 0.2%.

Figure 1B:
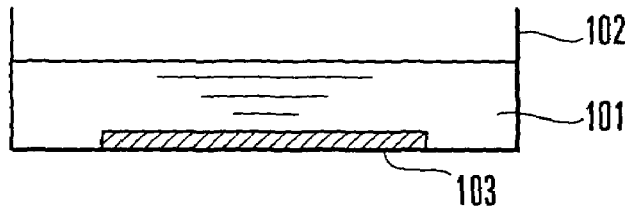

As shown in FIG. 1B, a porous material 103 is immersed in the solution 101. An example of the porous material 103 is porous glass having an average pore diameter of 4 nm. The first embodiment adopts Vycor 7930 available from Corning as the porous material 103. The size of the porous material is a chip size of 8 (mm)×8 (mm) with a thickness of 1 (mm).

Figure 1C:
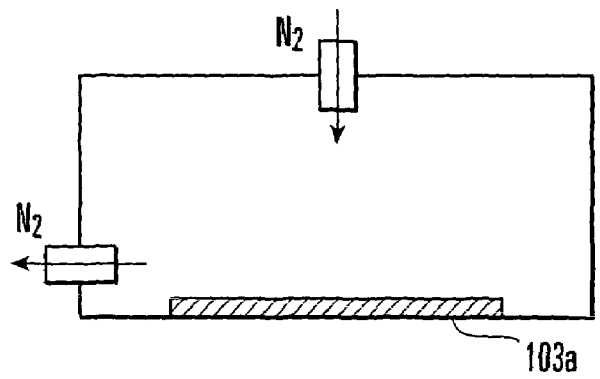

The porous material 103 is immersed in the solution 101 for 24 hrs to impregnate the pores of the porous material 103 with the solution. After that, the porous material 103 is air-dried. As shown in FIG. 1C, the porous material 103 is left dried in a nitrogen gas flow for 24 hrs or more, thereby fabricating a sensing element 103a.

An ozone gas detection method (measurement method) using the sensing element 103a will be described.

Figure 1D:
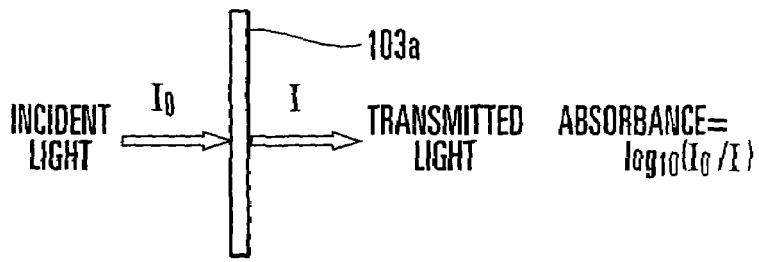
FIGS. 1D to 1F are views for explaining an ozone gas detection method according to the embodiment of the present invention.

As shown in FIG. 1D, the absorbance of the sensing element 103a in the direction of thickness is measured. In FIG. 1D, $I_0$ represents the light intensity of an incident light, and I represents the intensity of transmitted light. In this case, the absorbance is given by $\log_{10}(I_0/I)$.

Figure 1E:
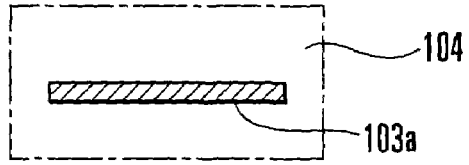
Figure 1F:
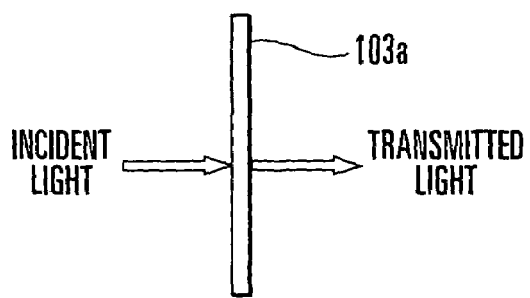

As shown in FIG. 1E, the sensing element 103a is exposed for a predetermined time, e.g., 3 hrs to detection target air 104 containing ozone at a concentration of, e.g., 100 ppb. Thereafter, the sensing element 103a is extracted from the detection target air 104. As shown in FIG. 1F, the absorbance of the sensing element 103a in the direction of thickness is measured again.

Figure 2:
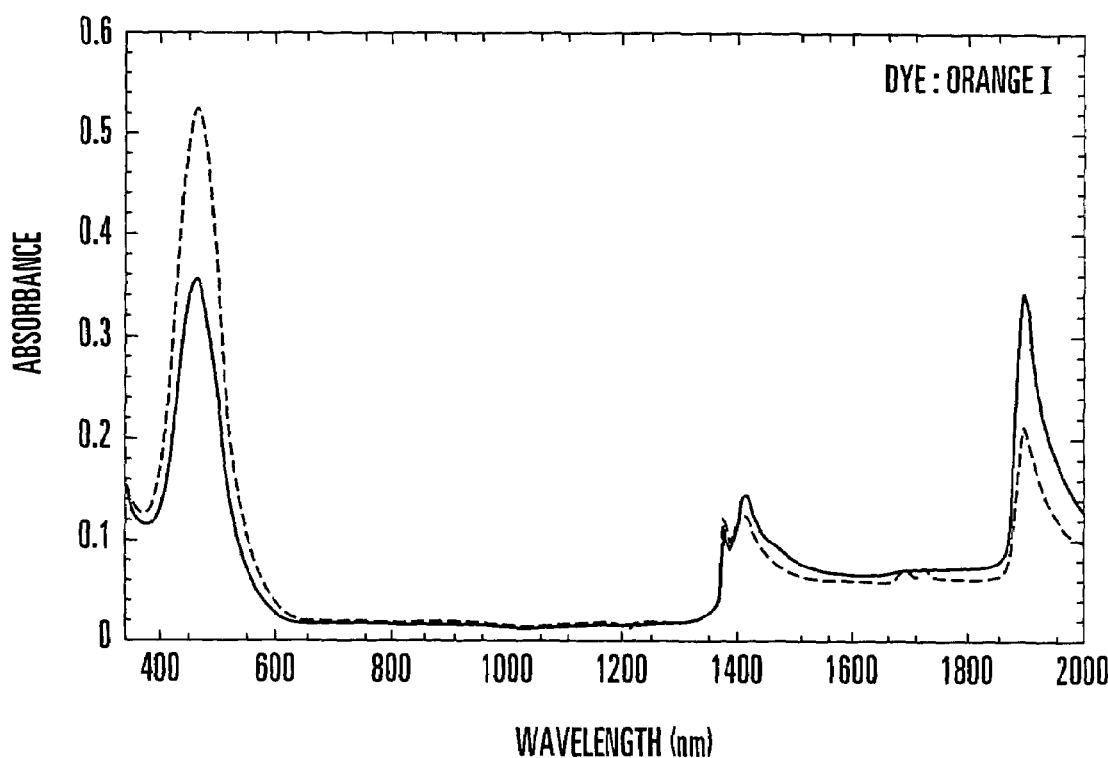
FIG. 2 is a graph showing the results of two absorbance measurements according to the embodiment of the present invention.

FIG. 2 shows the results of two absorbance measurements (absorbance analyses). In measurement, no absorbance is measured at a transmitted light measurement wavelength of 350 nm or less because light is absorbed by porous glass (Vycor 7930) which constitutes the sensing element.

In FIG. 2, the broken line represents the measurement result of the absorbance before exposure to detection target air, and the solid line represents the measurement result of the absorbance after exposure to detection target air. Both the solid and broken lines exhibit absorption of water around wavelengths of 1,350 nm and 1,900 nm. Absorption changes around wavelengths of 1,350 nm and 1,900 nm depending on the humidity of detection target air and the standing time of the sensing element. Hence, the effective measurement wavelength range of the ozone gas detection method (measurement method) using the sensing element 103a is determined to be 350 nm to 1,000 nm.

A large difference is found between the solid and broken lines in a wavelength range of 400 nm to 600 nm, particularly around 480 nm. Measurement of the absorbance after the sensing element 103a is exposed to detection target air exhibits a decrease in absorption at a wavelength of 480 nm. This means that, when the sensing element 103a is exposed to detection target air, the dye (stain) in the sensing element is decomposed to produce a new decomposition product. This product can be estimated to be produced by decomposing a diazo group contained in the molecular skeleton of Orange I.

In the first embodiment, ozone gas is detected by measuring a change in dye (stain) color before and after reaction with ozone.

The sensing element according to the first embodiment will be explained.

Figure 3:
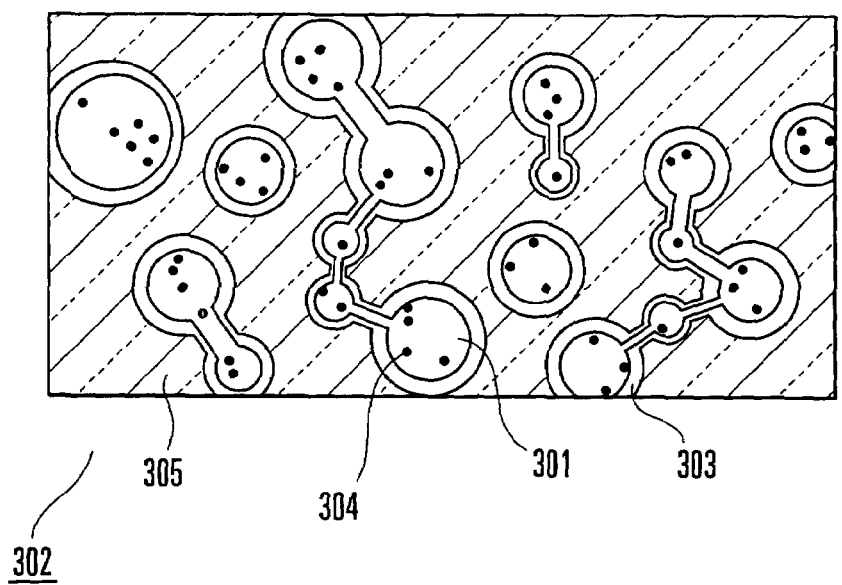
FIG. 3 is a schematic view showing the arrangement of a sensing element according to the embodiment of the present invention.

As shown in FIG. 3, a sensing element 302 fabricated by the above-described manufacturing method has a transparent matrix shape having a plurality of pores 301 with an average pore diameter of, e.g., 20 nm or less. The sensing element 302 functions as an adsorbent. At least some pores 301 in a porous material 305 are coupled to pores on the surface of the porous material.

The dye (stain) is deposited in the pore 301 of the sensing element 302. The porous material is exposed to air, and then moisture in air is adsorbed in the pore to form a thin water film. As a result, a thin film 303 of an aqueous solution (trapping and detective solution) in which the dye (stain) is dissolved can be estimated to be formed on the inner wall of the pore 301 of the sensing element 302. At least some pores 301 are coupled to pores on the surface of the porous material, so the dye can be estimated to be deposited in at least some pores.

An ozone molecule 304 which enters the pore 301 of the sensing element 302 reacts with the dye to decompose a diazo group. That is, the π-electron system extending over the molecule is split into two. The split molecule does not absorb any light around 480 nm, and the color of the sensing element 302 fades. That is, the dye causes fading reaction with ozone. At least some pores 301 are coupled to pores on the surface of the porous material, and ozone gas is estimated to react with the dye deposited in at least some pores.

A decomposed molecule can, therefore, be quantitatively measured by measuring the absorption spectrum of the sensing element by, e.g., a spectrophotometer (absorptiometer). By quantitative measurement, ozone gas can be indirectly measured.

For example, a porous material is made of a material which transmits light in the light absorption wavelength range of the dye. The light absorption characteristic of the sensing element which adsorbs ozone gas is measured. By measuring the light absorption characteristic, the adsorbed ozone gas can be detected.

As described above, the first embodiment executes measurement when the sensing element is exposed for 3 hrs to detection target air at an ozone concentration of 100 ppb. As a result of absorbance measurement, as shown in FIG. 2, a change in absorbance at a wavelength of 480 nm is as large as about 0.17, and ozone gas can be detected at high-sensitivity 100 ppb level.

The absorbance is measured by fixing the sensing element 103a to the thin film measurement holder of the absorptiometer. Quantitative measurement at ppb level can be achieved by obtaining the relationship between the difference in absorbance and the concentration from measurement of the absorbance.

A change in absorbance at the maximum absorption wavelength per exposure amount (concentration (ppb)×exposure time (h)) is obtained as the sensitivity index. In the first embodiment, as shown in FIG. 2, a change in absorbance after exposure to 100-ppb ozone gas for 3 hrs is 0.17. The sensitivity index is $5.7 \times 10^{-4}$ $ppb^{-1} \cdot hr^{-1}$, and very high sensitivity can be attained.

As described above, the first embodiment prepares a sensing element in which a dye that irreversibly changes in the absorbance of the visible region upon reaction with ozone gas is deposited in the pores of a transparent porous material. It is estimated that, when the sensing element is exposed to an ozone gas-containing atmosphere, a double bond such as a diazo group in the dye is broken by ozone gas adsorbed in the pores of the sensing element, and the electron state of the dye molecule changes to change the absorption spectrum of the visible region. Hence, ozone gas can be detected when the color of the sensing element changes and the first and second transmittances become different.

The first embodiment has exemplified the use of Orange I as a dye. Examples of a diazo dye are Orange II, Orange G, Methyl Orange, Bismarck Brown, Methyl Yellow, Acid Chrome Violet K, Crocein Orange G, Chromotrope FB, New Coccine, Crystal Scarlet, Alizarin Blue Black R, Plasmocorinth B, Sudan II, Sudan III, Sudan IV, Sudan Red B, Sudan Red 7B, Sunset Yellow FCF, Toluidine Red, Tropaeoline O, Xylidine Ponceau 2R, zincon monosodium salt, Benzopurpurin 4B, Biebrich Scarlet Red, Bordeaux R, Brilliant Crocein MOO, 2-(5-bromo-2-pyridylazo) 5-(diethylamino) phenol, 6'-butoxy-2,6-diamino-3,3'-azodipyridine, Acid Black 24, Acid Blue 29, Acid Blue 92, Acid Blue 113, Acid Blue 120, Acid Orange 8, Acid Orange 51, Acid Orange 63, Acid Orange 74, Acid Red 1, Acid Red 4, Acid Red 8, Acid Red 37, Acid Red 97, Acid Red 114, Acid Red 151, Acid Red 183, Acid Violet 7, Acid Yellow 17, Acid Yellow 25, Acid Yellow 29, Acid Yellow 34, Acid Yellow 42, Acid Yellow 76, Acid Yellow 99, Alizarin Yellow GG, Allura Red AC, Amaranth, Calcion, Chicago Sky Blue 6B, Chromotrope 2B, Chromotrope 2R, chrysoidin, Congo Red, Direct Blue 71, Direct Red 23, Direct Red 75, Direct Red 80, Direct Red 81, Direct Violet 51, Direct Yellow 50, Direct Yellow 62, Disperse Red 1, Disperse Red 19, Disperse Yellow 3, Eriochrome Blue Black B, Eriochrome Black T, Evans Blue, Fat Brown RR, Metanil Yellow, Naphthol Blue Black, Nitrazine Yellow, Nitro Red, Nitrosulfonazo III, Solvent Red 26, and Oil Red O. An example of a dye is a triphenylmethane stain (e.g., Malachite Green, Crystal Violet, or fuchsine). An example of a dye is an indigoid stain containing indigo (e.g., indigo or indigo carmine).

An example of a dye is a dye which is an aromatic compound (e.g., benzene, naphthalene, or anthracene) and has a diazo group. By using these dyes, ozone can be specifically detected even in the presence of another gas.

An example of a dye is a diazo dye which is an aromatic compound (e.g., benzene, naphthalene, or anthracene) and has a hydroxyl group, a sulfurous acid group, or primary to tertiary amino groups. By using these dyes, ozone can be specifically detected even in the presence of another gas. In addition, the stability of the dye can be obtained to more stably detect ozone.

As a method of introducing a dye into the pores of a porous material, the porous material is impregnated with the dye by using a solution, and the dye is introduced into pores and dried. As another method, the dye may be introduced into pores by vapor deposition. As still another method, the dye may be mixed with another compound and introduced into pores in fabricating a porous material by the sol-get method.

According to the first embodiment, the absorption area of ozone gas to be detected can be increased by using the sensing element 103a containing the dye in the pores of the porous material. Compared to a conventional method, the sensitivity and accumulation capacity can be increased, realizing cumulative use.

According to the first embodiment, the porous material which constitutes the sensing element 103a has a high transmittance in a wavelength region of about 350 nm to 1,000 nm. A change in the absorbance of the sensing element which is decomposed upon adsorption of ozone in the sensing element can be measured by measuring the transmittance of the sensing element. That is, absorbances of the sensing element before and after exposing the sensing element 103a to detection target air are measured and compared. As a result, ozone gas adsorbed in the sensing element 103a can be detected to easily detect ozone gas. In absorbance measurement, only a change in single peak suffices to be monitored, and measurement is easy.

In the sensing element according to the first embodiment, the light transmittance of the sensing element at a predetermined wavelength increases as the ozone gas concentration in measurement target air increases. The predetermined wavelength is about 480 nm in the case of the first embodiment.

The first embodiment can detect ozone gas from an optical change by using the compact sensing element 103a, and can very easily detect ozone gas at high precision.

Figure 5:
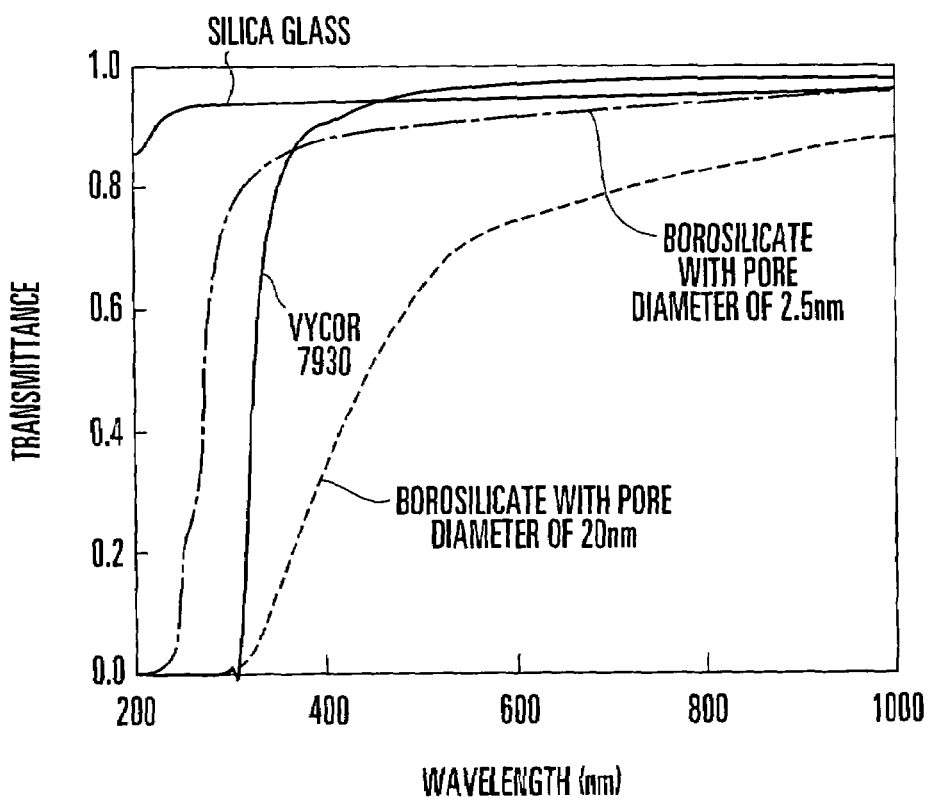
FIG. 5 is a correlation diagram showing the relationship between a glass porous material and the light transmittance.

As for the relationship between the porous material which constitutes the sensing element and its light transmittance, as shown in FIG. 5, when the sensing element is made of porous glass (borosilicate glass), light passes in the visible light region (350 nm to 800 nm) in measurement of the transmission spectrum in the UV visible wavelength region (wavelength: 200 nm to 2,000 nm) by setting the average pore diameter to 20 nm or less. For a larger average pore diameter, an abrupt decrease in transmittance in the visible region is observed.

In FIG. 5, the dotted line represents the transmittance of silica glass; the chain line, the transmittance of a borosilicate glass porous material having a pore diameter of 2.5 nm; the solid line, the transmittance of Vycor 7930 adopted in the first embodiment; and the broken line, the transmittance of a borosilicate glass porous material having a pore diameter of 20 nm.

Samples represented by the chain and broken lines are available from Geltec. The thicknesses of all samples used in the transmittance measurement method are 1 mm.

From the results shown in FIG. 5, the porous material preferably has an average pore diameter of 20 nm or less. The size of the dye is estimated to be 0.3 nm to 5 nm, and can be deposited in the pores of the porous material. A transparent porous material is preferably used in a visible range of 350 nm to 800 nm. In the first embodiment, the specific surface of the porous material is 100 m$^2$ or more per g.

Second Embodiment

An ozone gas sensing element according to the second embodiment of the present invention will be described.

An ozone gas sensing element fabrication method according to the second embodiment will be explained.

As shown in FIG. 1A, a solution obtained by dissolving sodium carbonate in water is prepared as an alkali solution. The sodium carbonate concentration is 5%.

As shown in FIG. 1B, a porous material having an average pore diameter of 4 nm is dipped in the alkali solution for a predetermined time, e.g., 2 hrs, and then cleaned with pure water.

This porous material is identical to that described in the first embodiment, and is made of Vycor 7930 available from Corning. The porous material has a chip size of 8 (mm)×8 (mm) with a thickness of 1 (mm).

A solution is prepared by dissolving fuchsine in ethanol. The fuchsine concentration is 0.002%. The porous material which has been dipped in the alkali solution and cleaned with pure water is immersed in the fuchsine ethanol solution for 2 hrs to impregnate the solution into the pores of the porous material. Thereafter, the porous material is air-dried, and left dried in a nitrogen gas flow for half a day or more. Consequently, a sensing element according to the second embodiment is fabricated.

In the above-described fabrication method, a comparative sensing element is fabricated by dipping a porous material in pure water instead of an alkali solution and then in a fuchsine solution. The absorbances of the sensing element according to the second embodiment and the comparative sensing element fabricated in the above manner are measured.

Figure 6:
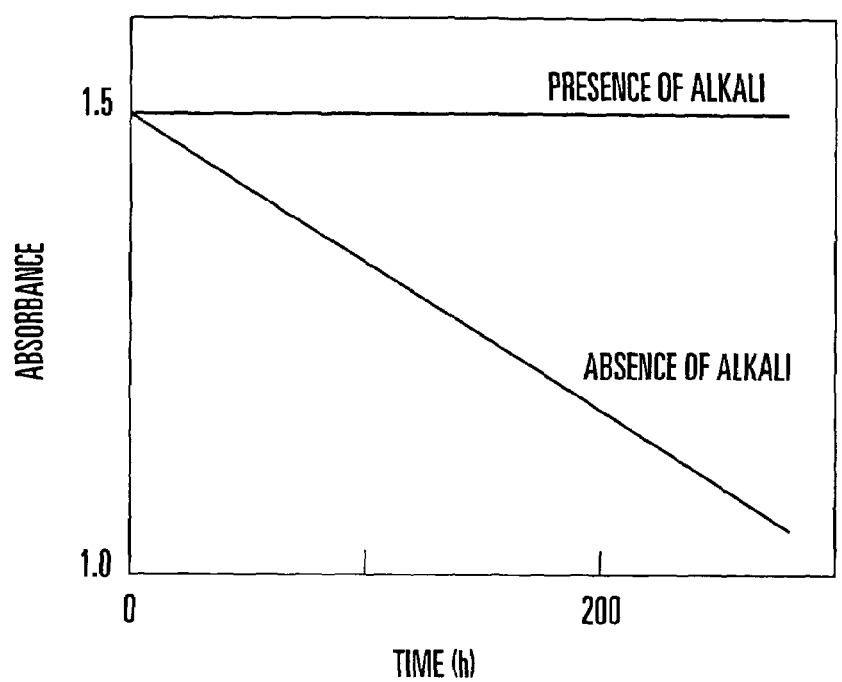
FIG. 6 is a graph showing the characteristic of a sensing element according to the second embodiment of the present invention.

A change in absorbance at 545 nm upon when the sensing element according to the second embodiment and the comparative sensing element are left to stand in nitrogen gas will be explained with reference to FIG. 6.

The absorbance of the comparative sensing element which does not undergo alkali treatment changes even in nitrogen. To the contrary, the absorbance of the sensing element according to the second embodiment which undergoes alkali treatment is stable without any change.

Figure 7:
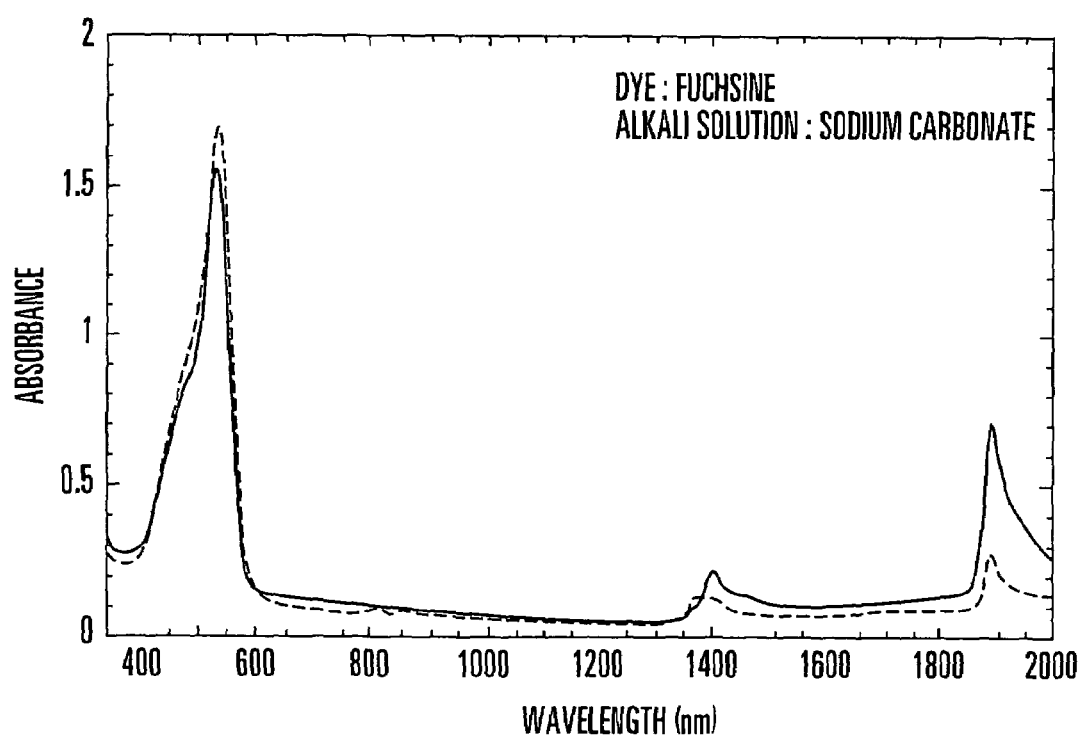
FIG. 7 is a graph showing the results of two absorbance measurements in an ozone gas detection method according to the second embodiment of the present invention.

A change in absorption spectrum before and after exposing, to measurement target air, the sensing element according to the second embodiment that has undergone alkali treatment will be described with reference to FIG. 7. In FIG. 7, the broken line represents the absorption spectrum before exposing the sensing element of the second embodiment to air. The solid line represents the absorption spectrum after exposing the sensing element of the second embodiment for 24 hrs to air containing ozone gas at a concentration of 100 ppb.

In FIG. 7, the sensing element of the second embodiment represented by the solid line exhibits a decrease in absorption at a wavelength of 545 nm. This is estimated to occur because fuchsonimine in the fuchsine molecule is decomposed by ozone, i.e., the $\pi$-electron system is split.

The absorbance change is as large as about 0.1, and ozone gas can be detected at high-sensitivity ppb level even by ozone gas detection using the sensing element of the second embodiment.

Referring to FIG. 7, the sensitivity index is obtained to be $4.2 \times 10^{-5}$ ppb$^{-1} \cdot$hr$^{-1}$, and very high sensitivity can be attained.

As described above, the second embodiment prepares a sensing element in which a mixture of alkali and a dye (stain) that changes in the absorbance of the visible region upon reaction with ozone gas is deposited in the pores of a transparent porous material. It is estimated that, when the sensing element is exposed to an ozone gas-containing atmosphere, a double bond such as C=C in the dye is broken by ozone gas adsorbed in the pores of the sensing element, and the electron state of the dye molecule changes to change the absorption spectrum of the visible region. Ozone gas can, therefore, be detected when the color of the sensing element changes and the first and second transmittances become different.

The second embodiment has exemplified the use of fuchsine as a dye. An example of a dye is a triphenylmethane stain (e.g., Malachite Green or Crystal Violet).

As a method of introducing a dye into the pores of a porous material, the porous material is impregnated with the dye by using a trapping and detective solution, and the dye is introduced into pores and dried. As another method, the dye may be introduced into pores by vapor deposition. As still another method, the dye may be mixed with another compound and introduced into pores in fabricating a porous material by the sol-get method.

According to the second embodiment, the adsorption area of ozone gas to be detected can be increased by using a sensing element 103a containing the dye in the pores of the porous material. Compared to a conventional method, the sensitivity and accumulation capacity can be increased, realizing cumulative use.

The second embodiment has exemplified the use of an aqueous solution prepared by dissolving sodium carbonate in water as an alkali solution. Examples of alkali are an alkali itself and alkali salt. A desirable example of an alkali salt is a salt of a weak acid and a strong alkali.

Also in the second embodiment, the porous material preferably has an average pore diameter of 20 nm or less.

Third Embodiment

An ozone gas sensing element according to the third embodiment of the present invention will be described.

An ozone gas sensing element fabrication method according to the third embodiment will be explained.

As shown in FIG. 1A, a solution is prepared by dissolving, in water, Methyl Orange as a dye (stain) and triethanolamine as an acid gas sorbent. The Methyl Orange concentration is 0.35%, and the triethanolamine concentration is 1.0%.

As shown in FIG. 1B, a porous material having an average pore diameter of 4 nm is immersed in the solution. The porous material is identical to that described in the first embodiment, and is made of Vycor 7930 available from Corning. The porous material has a chip size of 8 (mm)×8 (mm) with a thickness of 1 (mm).

The porous material is immersed in the solution for 2 hrs to impregnate the pores of the porous material with the solution. The porous material is air-dried, and left dried in a nitrogen gas flow for half a day, thereby fabricating a sensing element according to the third embodiment.

Figure 8:
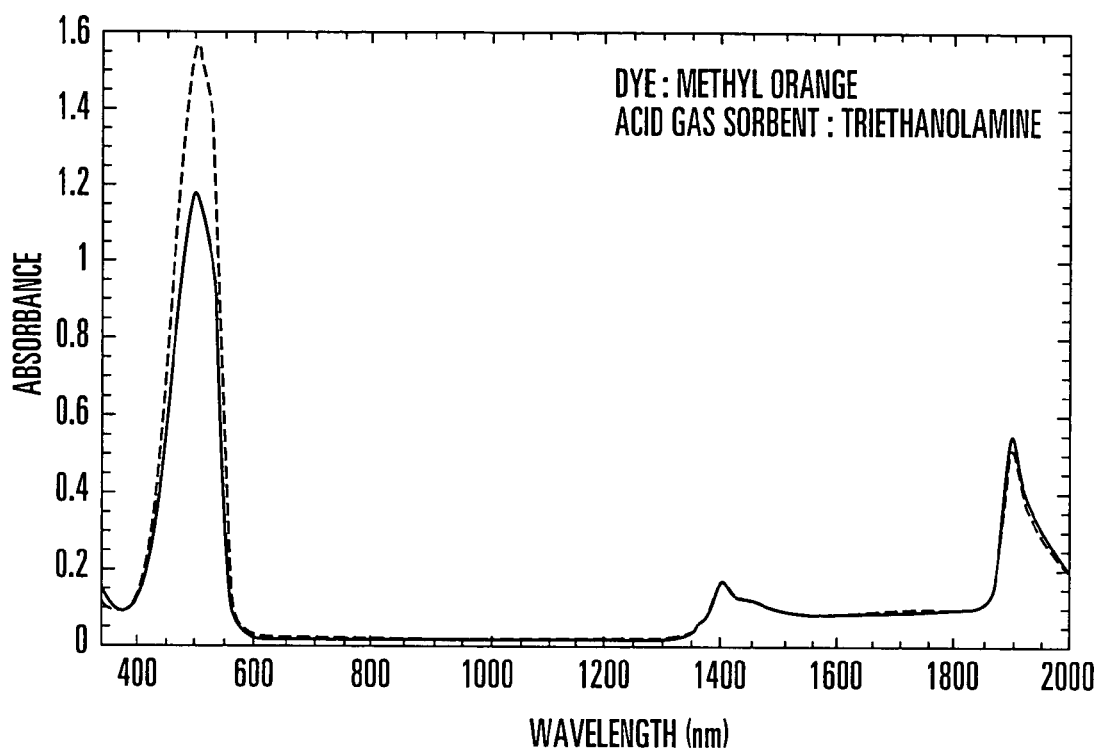
FIG. 8 is a graph showing the results of two absorbance measurements in an ozone gas detection method according to the third embodiment of the present invention.

Absorption spectra before and after exposing the sensing element of the third embodiment to measurement target air will be described with reference to FIG. 8. In FIG. 8, the broken line represents the absorption spectrum before exposure to measurement target air. The solid line represents the absorption spectrum after the sensing element of the third embodiment is exposed for 24 hrs to air containing ozone gas at a concentration of 100 ppb.

As shown in FIG. 8, the sensing element of the third embodiment exhibits a decrease in absorption around a wavelength of 510 nm. This decrease is about 0.3, and ozone gas can be detected at high-sensitivity ppb level.

Referring to FIG. 8, the sensitivity index is obtained to be $1.3 \times 10^{-4}$ $ppb^{-1} \cdot hr^{31\ 1}$.

In the above-described fabrication method, a comparative sensing element was fabricated except triethanolamine. The influence of disturbance of $NO_2$ as an acid gas was investigated using the comparative sensing element. As a result, the comparative sensing element observed disturbance of $NO_2$, but the sensing element of the third embodiment did not observe any disturbance of $NO_2$.

As described above, the third embodiment prepares a sensing element in which a mixture of an acid gas sorbent and a dye (stain) that changes in the absorbance of the visible region upon reaction with ozone gas is deposited in the pores of a transparent porous material. It is estimated that, when the sensing element is exposed to an atmosphere containing ozone gas and many acid gases other than ozone gas, a double bond such as N=N in the dye is broken by ozone gas adsorbed in the pores of the sensing element almost free from disturbance of an acid gas, and the electron state of the dye molecule changes to change the absorption spectrum of the visible region. Ozone gas can, therefore, be detected when the color of the sensing element changes and the first and second transmittances become different.

The third embodiment has exemplified the use of Methyl Orange as a dye. Examples of a dye are Orange I, Orange II, Orange G, Bismarck Brown, Methyl Yellow, Acid Chrome Violet K, Crocein Orange G, Chromotrope FB, New Coccine, Crystal Scarlet, Alizarin Blue Black R, Plasmocorinth B, Sudan II, Sudan III, Sudan IV, Sudan Red B, Sudan Red 7B, Sunset Yellow FCF, Toluidine Red, Tropaeoline O, Xylidine Ponceau 2R, zincon monosodium salt, Benzopurpurin 4B, Biebrich Scarlet Red, Bordeaux R, Brilliant Crocein MOO, 2-(5-bromo-2-pyridylazo) 5-(diethylamino) phenol, 6'-butoxy-2,6-diamino-3,3'-azodipyridine, Acid Black 24, Acid Blue 29, Acid Blue 92, Acid Blue 113, Acid Blue 120, Acid Orange 8, Acid Orange 51, Acid Orange 63, Acid Orange 74, Acid Red 1, Acid Red 4, Acid Red 8, Acid Red 37, Acid Red 97, Acid Red 114, Acid Red 151, Acid Red 183, Acid Violet 7, Acid Yellow 17, Acid Yellow 25, Acid Yellow 29, Acid Yellow 34, Acid Yellow 42, Acid Yellow 76, Acid Yellow 99, Alizarin Yellow GG, Allura AC, Amaranth, Calcion, Chicago Sky Blue 6B, Chromotrope 2B, Chromotrope 2R, chrysoidin, Congo Red, Direct Blue 71, Direct Red 23, Direct Red 75, Direct Red 80, Direct Red 81, Direct Violet 51, Direct Yellow 50, Direct Yellow 62, Disperse Red 1, Disperse Red 19, Disperse Yellow 3, Eriochrome Blue Black B, Eriochrome Black T, Evans Blue, Fat Brown RR, Metanil Yellow, Naphthol Blue Black, Nitrazine Yellow, Nitro Red, Ntirosulfonazo III, Solvent Red 26, and Oil Red O. An example of a dye is a triphenylmethane stain (e.g., Malachite Green, Crystal Violet, or fuchsine).

An example of a dye is a dye which is an aromatic compound (e.g., benzene, naphthlene, or anthracene) and has a diazo group. By using these dyes, ozone can be specifically detected even in the presence of another gas.

An example of a dye is a diazo dye which is an aromatic compound (e.g., benzene, naphthalene, or anthracene) and has a hydroxyl group, a sulfurous acid group, or primary to tertiary amino groups. By using these dyes, ozone can be specifically detected even in the presence of another gas. In addition, the stability of the dye can be obtained to more stably detect ozone.

As a method of introducing a dye into a porous material, the porous material is impregnated with the dye by using a solution, and the dye is introduced into pores and dried. As another method, the dye may be introduced into pores by vapor deposition. As still another method, the dye may be mixed with another compound and introduced into pores in fabricating a porous material by the sol-get method.

According to the third embodiment, the adsorption area of ozone gas to be detected can be increased by using a sensing element 103a containing the dye in the pores of the porous material. Compared to a conventional method, the sensitivity and accumulation capacity can be increased, realizing cumulative use.

The third embodiment has exemplified the use of triethanolamine as an acid gas sorbent. Alternatively, glycerol may be used.

Also in the third embodiment, the porous material preferably has an average pore diameter of 20 nm or less.

Fourth Embodiment

An ozone gas sensing element according to the fourth embodiment of the present invention will be described.

An ozone gas sensing element fabrication method according to the fourth embodiment will be explained.

As shown in FIG. 1A, a solution is prepared by dissolving Orange II as a dye (stain) in water. The Orange II concentration is 0.2%. The trapping and detective solution is filled in a vessel 102. As shown in FIG. 1B, a porous material having an average pore diameter of 4 nm is immersed for about 2 hrs. The porous material is identical to that described in the first embodiment, and is made of Vycor 7930 available from Corning. The porous material has a chip size of 8 (mm)×8 (mm) with a thickness of 1 (mm).

The porous material is immersed in the solution to impregnate the solution into the porous material. The porous material impregnated with the solution is extracted from the solution, air-dried, and left dried in a nitrogen gas flow for half a day, thereby fabricating a sensing element according to the fourth embodiment.

When the fabricated sensing element was exposed to air at an ozone concentration of 100 ppb, the orange color visually faded. This change was measured by an absorptiometer.

Figure 9:
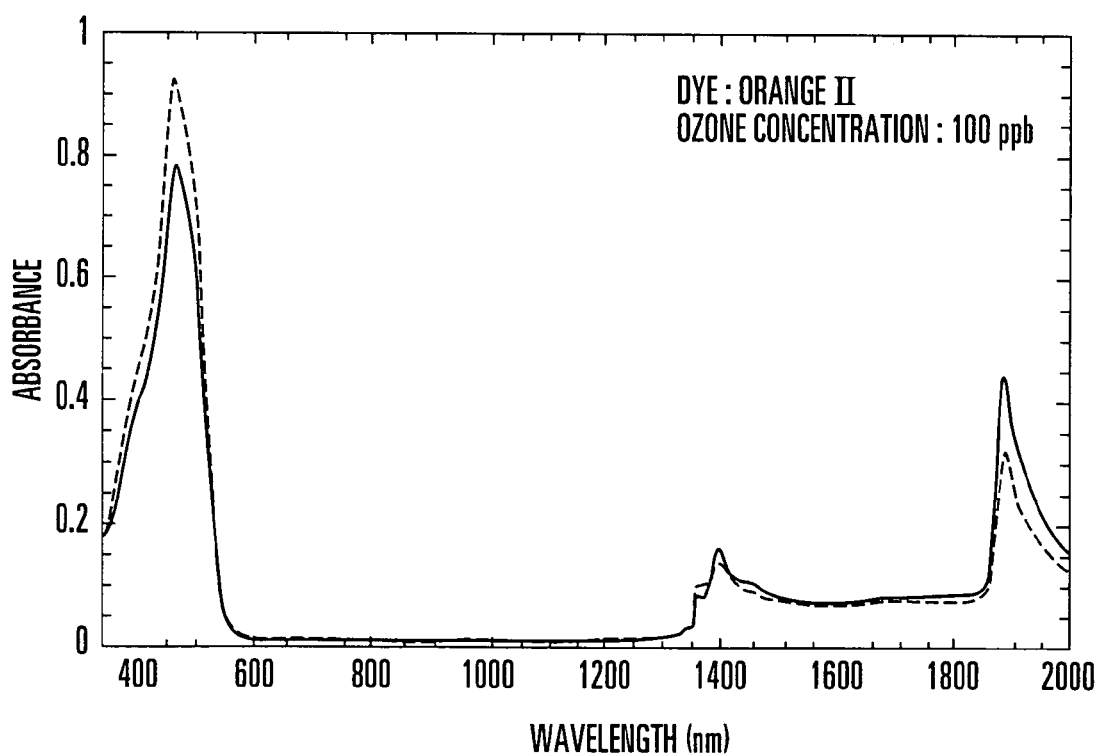
FIG. 9 is a graph showing the results of two absorbance measurements in an ozone gas detection method according to the fourth embodiment of the present invention.

The result of measuring the absorbance of the sensing element according to the fourth embodiment will be explained with reference to FIG. 9. In FIG. 9, the broken line represents the measurement result of the sensing element in initial dark orange, and the solid line represents the measurement result of the sensing element after fading. This change was irreversible. The ozone concentration was changed within the range of 100 ppb to 1 ppm to observe almost the same spectrum change except for the light absorption intensity.

Figure 10:
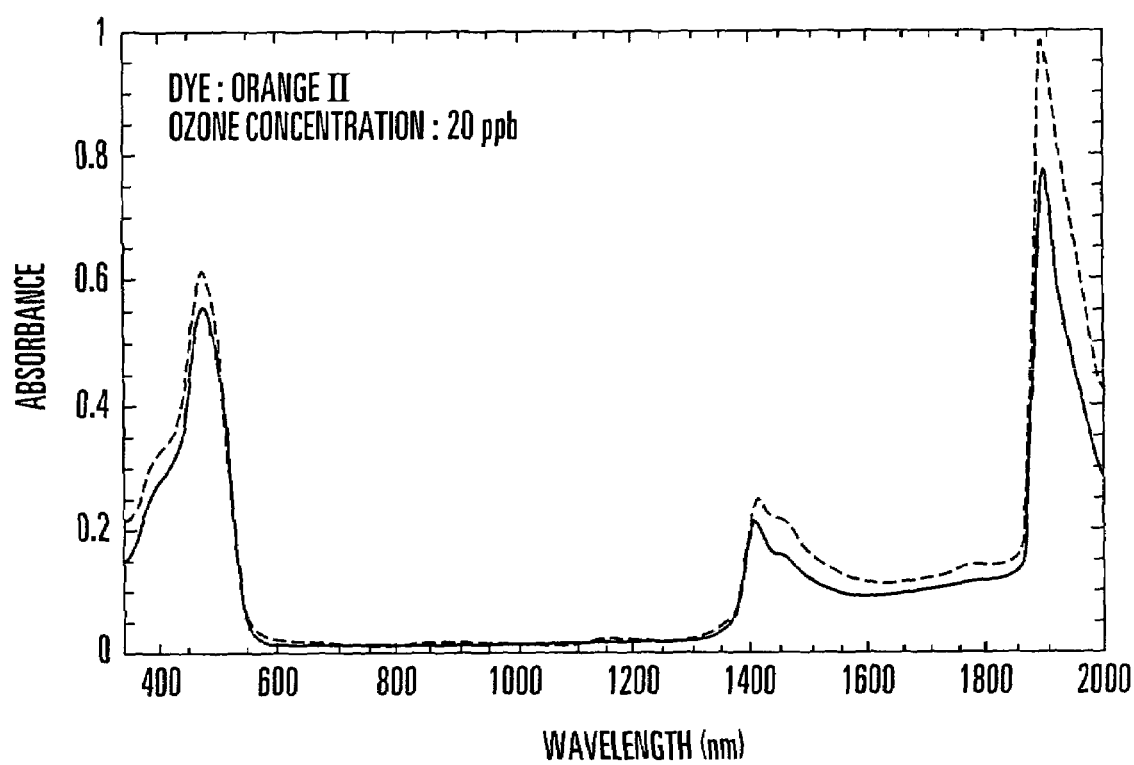
FIG. 10 is a graph showing the results of two absorbance measurements in another ozone gas detection method according to the fourth embodiment of the present invention.

FIG. 10 shows the absorbance when the sensing element is exposed to air at an ozone concentration of about 20 ppb. In FIG. 10, the broken line represents the measurement result of the sensing element in initial dark orange, and the solid line represents the measurement result after exposure to detection target air. This change was also irreversible.

As shown in FIG. 10, the sensing element according to the fourth embodiment exhibits a decrease in absorption around a wavelength of 510 nm. Ozone gas can be detected even in the use of the sensing element according to the fourth embodiment. Ozone gas in air can also be detected.

The fourth embodiment has exemplified the use of Orange II as a dye. Examples of a dye are Orange I, Orange G, Methyl Orange, Bismarck Brown, Methyl Yellow, Acid Chrome Violet K, Crocein Orange G, Chromotrope FB, New Coccine, Crystal Scarlet, Alizarin Blue Black R, Plasmocorinth B, Sudan II, Sudan III, Sudan IV, Sudan Red B, Sudan Red 7B, Sunset Yellow FCF, Toluidine Red, Tropaeoline O, Xylidine Ponceau 2R, zincon monosodium salt, Benzopurpurin 4B, Biebrich Scarlet Red, Bordeaux R, Brilliant Crocein MOO, 2-(5-bromo-2-pyridylazo) 5-(diethylamino) phenol, 6'-butoxy-2,6-diamino-3,3'-azodipyridine, Acid Black 24, Acid Blue 29, Acid Blue 92, Acid Blue 113, Acid Blue 120, Acid Orange 8, Acid Orange 51, Acid Orange 63, Acid Orange 74, Acid Red 1, Acid Red 4, Acid Red 8, Acid Red 37, Acid Red 97, Acid Red 114, Acid Red 151, Acid Red 183, Acid Violet 7, Acid Yellow 17, Acid Yellow 25, Acid Yellow 29, Acid Yellow 34, Acid Yellow 42, Acid Yellow 76, Acid Yellow 99, Alizarin Yellow GG, Allura Red AC, Amaranth, Calcion, Chicago Sky Blue 6B, Chromotrope 2B, Chromotrope 2R, chrysoidin, Congo Red, Direct Blue 71, Direct Red 23, Direct Red 75, Direct Red 80, Direct Red 81, Direct Violet 51, Direct Yellow 50, Direct Yellow 62, Disperse Red 1, Disperse Red 19, Disperse Yellow 3, Eriochrome Blue Black B, Eriochrome Black T, Evans Blue, Fat Brown RR, Metanil Yellow, Naphthol Blue Black, Nitrazine Yellow, Nitro Red, Nitrosulfonazo III, Solvent Red 26, and Oil Red O. An example of a dye is a dye which is an aromatic compound (e.g., benzene, naphthalene, or anthracene) and has a diazo group. By using these dyes, ozone can be specifically detected even in the presence of another gas.

An example of a dye is a diazo dye which contains a dye as an aromatic compound (e.g., benzene, naphthalene, or anthracene) having a diazo group and has a hydroxyl group, a sulfurous acid group, or primary to tertiary amino groups. By using these dyes, ozone can be specifically detected even in the presence of another gas. In addition, the stability of the dye can be obtained to more stably detect ozone.

As a method of introducing a dye into the pores of a porous material, the porous material is impregnated with the dye by using a trapping and detective solution, and the dye is introduced into pores and dried. As another method, the dye may be introduced into pores by vapor deposition. As still another method, the dye may be mixed with another compound and introduced into pores in fabricating a porous material by the sol-get method.

According to the fourth embodiment, the adsorption area of ozone gas to be detected can be increased by using a sensing element 103a containing the dye in the pores of the porous material. Compared to a conventional method, the sensitivity and accumulation capacity can be increased, realizing cumulative use.

Also in the fourth embodiment, the porous material preferably has an average pore diameter of 20 nm or less.

Fifth Embodiment

An ozone gas sensing element according to the fifth embodiment of the present invention will be described.

An ozone gas sensing element fabrication method according to the fifth embodiment will be explained.

As shown in FIG. 1A, an aqueous solution of 0.3% of indigo carmine disodium salt and 1 N of hydrochloric acid is prepared as a solution 101 by dissolving indigo carmine disodium salt as a dye (stain) in water and adding hydrochloric acid as an acid. The solution 101 is filled in a vessel 102.

As shown in FIG. 1B, a porous material 103 is immersed in the solution 101. An example of the porous material 103 is porous glass having an average pore diameter of 4 nm. The porous material 103 is identical to that described in the first embodiment, and is made of Vycor 7930 available from Corning. The porous material has a chip size of 8 (mm)×8 (mm) with a thickness of 1 (mm).

The porous material 103 is immersed in the solution 101 for 24 hrs to impregnate the pores of the porous material 103 with the solution 101. The porous material impregnated with the solution 101 is extracted from the solution, and air-dried. As shown in FIG. 1C, the porous material is left dried in a nitrogen gas flow for 24 hrs or more, thereby fabricating a sensing element 103a according to the fifth embodiment.

As shown in FIG. 1D, the absorbance of the sensing element 103a in the direction of thickness is measured. In FIG. 1E, the sensing element 103a is exposed for 2 hrs to detection target air 104 containing ozone at a concentration of, e.g., 20 ppb. The sensing element 103a is extracted from the detection target air 104. As shown in FIG. 1F, the absorbance of the sensing element 103a in the direction of thickness is measured again.

The result of two absorbance measurements (absorbance analyses) will be explained with reference to FIG. 11. No absorbance is measured at a transmitted light measurement wavelength of 350 nm or less because light is absorbed by porous glass (Vycor 7930) which constitutes the sensing element.

In FIG. 11, the broken line represents the absorbance before exposure to detection target air. The solid line represents the absorbance after exposure to detection target air. A large difference is found between the solid and broken lines in a wavelength range of 500 nm to 700 nm, particularly around 600 nm. In measurement of the absorbance after exposure to detection target air, absorption decreases at a wavelength of 600 nm. The absorbance can be estimated to decrease because the dye in the sensing element is decomposed to produce a new decomposition product upon exposure to detection target air. This product can be estimated to be produced by decomposing a C═C bond contained in the molecular skeleton of indigo carmine disodium salt.

The absorbance of the sensing element at 600 nm obtained when no hydrochloric acid is added to the trapping and detective solution is 1/100 of the absorbance of the sensing element at 600 nm obtained when hydrochloric acid is added to the solution. Addition of hydrochloric acid increases the absorbance around 600 nm. Many dye components are estimated to enter the porous material.

As shown in FIG. 3, a sensing element fabricated by the above-described manufacturing method functions as an adsorbent having a transparent matrix shape with a plurality of pores 301 at an average pore diameter of, e.g., 20 nm or less. At least some pores 301 in a porous material 305 are coupled to pores on the surface of the porous material. The dye is deposited in the pore 301 of a sensing element 302. The porous material is exposed to air, and then moisture in air is adsorbed in the pore to form a thin water film. As a result, a thin film 303 of an aqueous solution (trapping and detective solution) in which the dye is dissolved can be estimated to be formed on the inner wall of the pore 301 of the sensing element 302. At least some pores 301 are coupled to pores on the surface of the porous material, so the dye can be estimated to be deposited in at least some pores.

An ozone molecule 304 which enters the pore 301 of the sensing element 302 reacts with the dye to decompose a carbon-carbon double bond. That is, the π-electron system extending over the molecule is split into two or more. The split molecule does not absorb any light around 600 nm, and the color of the sensing element fades. That is, the dye causes fading reaction with ozone. At least some pores 301 are coupled to pores on the surface of the porous material, and ozone gas is estimated to react with the dye deposited in at least some pores.

The absorption spectrum is measured using, e.g., a spectrophotometer (absorptiometer) to achieve quantitative measurement of the decomposed molecule. By quantitative measurement, ozone gas can be indirectly measured.

For example, a porous material is made of a material which transmits light in the light absorption wavelength region of the dye. The light absorption characteristic of the sensing element which adsorbs ozone gas can be measured. By measuring the light absorption characteristic, the adsorbed ozone gas can be detected.

Similar to the method described in the first embodiment, the absorbance can be measured by fixing the sensing element 103a of the fifth embodiment to the thin film measurement holder of the absorptiometer. Quantitive measurement at ppb level can be achieved by obtaining the relationship between the difference in absorbance and the concentration from measurement of the absorbance.

As described in the first embodiment, a change in absorbance at the maximum absorption wavelength per exposure amount (concentration (ppb)×exposure time (h)) is obtained as the sensitivity index. As shown in FIG. 11, a change in absorbance after exposure to 20-ppb ozone gas for 2 hrs is 0.009. The sensitivity index is $2.5 \times 10^{-4}$ $ppb^{-1} \cdot hr^{-1}$, and very high sensitivity can be attained.

As described above, the fifth embodiment prepares a sensing element in which a mixture of an acid and a dye (stain) that changes in the absorbance of the visible region upon reaction with ozone gas is deposited in the pores of a transparent porous material. It is estimated that, when the sensing element is exposed to and ozone gas-containing atmosphere, a double bond such as C=C in the dye is broken by ozone gas absorbed in the pores of the sensing element, and the structure and electron state of the dye molecule change to change the absorption spectrum of the visible region. Thus, ozone gas can be detected when the color of the sensing element changes and the first and second transmittances become different.

The fifth embodiment has exemplified the use of indigo carmine disodium salt as a dye. An example of a dye is an indigoid stain having indigo (e.g., indigo or indigo carmine tripotassium salt).

Examples of a dye are Orange I, Orange II, Orange G, Methyl Orange, Bismarck Brown, Methyl Yellow, Acid Chrome Violet K, Crocein Orange G, Chromotrope FB, New Coccine, Crystal Scarlet, Alizarin Blue Black R, Plasmocorinth B, Sudan II, Sudan III, Sudan IV, Sudan Red B, Sudan Red 7B, Sunset Yellow FCF, Toluidine Red, Tropaeoline O, Xylidine Ponceau 2R, zincon monosodium salt, Benzopurpurin 4B, Biebrich Scarlet Red, Bordeaux R, Brilliant Crocein MOO, 2-(5-bromo-2-pyridylazo) 5-(diethylamino) phenol, 6'-butoxy-2,6-diamino-3,3'-azodipyridine, Acid Black 24, Acid Blue 29, Acid Blue 92, Acid Blue 113, Acid Blue 120, Acid Orange 8, Acid Orange 51, Acid Orange 63, Acid Orange 74, Acid Red 1, Acid Red 4, Acid Red 8, Acid Red 37, Acid Red 97, Acid Red 114, Acid Red 151, Acid Red 183, Acid Violet 7, Acid Yellow 17, Acid Yellow 25, Acid Yellow 29, Acid Yellow 34, Acid Yellow 42, Acid Yellow 76, Acid Yellow 99, Alizarin Yellow GG, Allura Red AC, Amaranth, Calcion, Chicago Sky Blue 6B, Chromotrope 2B, Chromotrope 2R, chrysoidin, Congo Red, Direct Blue 71, Direct Red 23, Direct Red 75, Direct Red 80, Direct Red 81, Direct Violet 51, Direct Yellow 50, Direct Yellow 62, Disperse Red 1, Disperse Red 19, Disperse Yellow 3, Eriochrome Blue Black B, Eriochrome Black T, Evans Blue, Fat Brown RR, Metanil Yellow, Naphthol Blue Black, Nitrazine Yellow, Nitro Red, Nitrosulfonazo III, Solvent Red 26, and Oil Red O. An example of a dye is a dye which is an aromatic compound (e.g., benzene, naphthalene, or anthracene) and has a diazo group. By using these dyes, ozone can be specifically detected even in the presence of another gas.

An example of a dye is a diazo dye which contains a dye as an aromatic compound (e.g., benzene, naphthalene, or anthracene) having a diazo group and has a hydroxyl group, and has a hydroxyl group, a sulfurous acid group, or primary to tertiary amino groups. By using these dyes, ozone can be specifically detected even in the presence of another gas. In addition, the stability of the dye can be obtained to more stably detect ozone.

As a method of introducing a dye into the pores of a porous material, the porous material is impregnated with the dye serving as a solution, and the dye is introduced into pores and dried. As another method, the dye may be introduced into pores by vapor deposition. As still another method, the dye may be mixed with another compound and introduced into pores in fabricating a porous material by the sol-get method.

According to the fifth embodiment, the adsorption area of ozone gas to be detected can be increased by using the sensing element containing the dye in the pores of the porous material. Compared to a conventional method, the sensitivity and accumulation capacity can be increased, realizing cumulative use.

Figure 4:
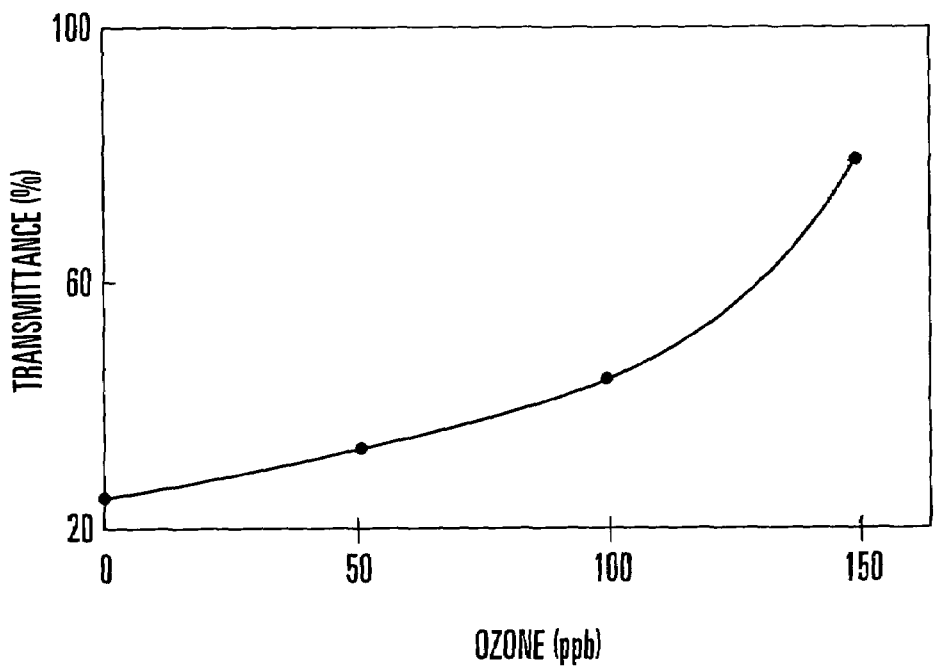
FIG. 4 is a correlation diagram showing the relationship between the ozone concentration and the transmittance in a sensing element according to the first embodiment.

According to the fifth embodiment, as shown in FIG. 4, the light transmittance of the sensing element at a predetermined wavelength increases as the ozone gas concentration in measurement target air increases. The predetermined wavelength is about 600 nm.

The fifth embodiment can detect ozone gas from an optical change by using the compact sensing element 103a, and can very easily detect ozone gas at high precision. In absorbance measurement, only a change in single peak suffices to be monitored, and measurement is easy.

When the sensing element was made of porous glass (borosilicate glass), light passed in the visible light region (350 nm to 800 nm) in measurement of the transmission spectrum in the UV visible wavelength region (wavelength: 200 nm to 2,000 nm) by setting the average pore diameter to 20 nm or less. For a larger average pore diameter, an abrupt decrease in transmittance in the visible region was observed. Hence, the above-described porous material desirably has an average pore diameter of 20 nm or less. A transparent porous material is desirably used in a visible region of 350 nm to 800 nm. In the fifth embodiment, the specific surface of the porous material is 100 $m^2$ or more per g.

In the fifth embodiment, the solution 101 is prepared by adding hydrochloric acid as an acid. Any one of acetic acid, sulfuric acid, and phosphoric acid may be used.

Sixth Embodiment

An ozone gas sensing element according to the sixth embodiment of the present invention will be described.

An ozone gas sensing element fabrication method according to the sixth embodiment will be explained.

As shown in FIG. 1A, a solution is prepared by dissolving, in water, indigo carmine disodium salt as a dye (stain), and hydrochloric acid and glycerol as an acid gas sorbent. The indigo carmine disodium salt concentration is 0.4%, the hydrochloric acid concentration is 1 N, and the glycerol concentration is 1.0%.

As shown in FIG. 1B, a porous material having an average pore diameter of 4 nm is immersed in the dye solution. The porous material is identical to that described in the first embodiment, and is made of Vycor 7930 available from Corning. The porous material has a chip size of 8 (mm)×8 (mm) with a thickness of 1 (mm).

The porous material is immersed in the dye solution for 24 hrs to impregnate the pores of the porous material with the dye solution. The porous material is air-dried, and then left dried in a dry air flow for a day, thereby fabricating a sensing element according to the sixth embodiment.

The absorbance of the sensing element fabricated in this manner according to the sixth embodiment was measured.

Absorption spectra before and after exposing the sensing element of the sixth embodiment to measurement target air will be described with reference to FIG. 12. In FIG. 12, the broken line represents the absorption spectrum before exposure to measurement target air. The solid line represents the absorption spectrum after exposure for 2 hrs to air containing ozone gas at a concentration of 100 ppb.

As shown in FIG. 12, the sensing element of the sixth embodiment represented by the solid line exhibits a decrease in absorption around a wavelength of 600 nm. This decrease is about 0.05, and ozone gas can be detected at high-sensitivity ppb level.

In the above-described fabrication method, a comparative sensing element was fabricated except glycerol. The influence of disturbance of $NO_2$ as an acid gas was investigated using the comparative sensing element. As a result, the comparative sensing element observed disturbance of $NO_2$, but the sensing element of the sixth embodiment did not observe any disturbance of $NO_2$.

As described above, the sixth embodiment prepares a sensing element in which a mixture of an acid, glycerol, and a dye that changes in the absorbance of the visible region upon reaction with ozone gas is deposited in the pores of a transparent porous material. It is estimated that, when the sensing element is exposed to an atmosphere containing ozone gas and many acid gases other than ozone, a carbon-carbon double bond in an indigo ring contained in the dye is broken by ozone gas deposited in the pores of the sensing element almost free from disturbance of an acid gas, and the electron state of the dye molecule changes to change the absorption spectrum of the visible region. For this reason, ozone gas can be detected when the color of the sensing element changes and the first and second transmittances become different.

The sixth embodiment has exemplified the use of indigo carmine disodium salt as a dye. An example of a dye is an indigoid stain having indigo (e.g., indigo or indigo carmine tripotassium salt).

As a method of introducing a dye into the pores of a porous material, the porous material is impregnated with the dye serving as a solution and dried. As another method, the dye may be introduced into pores by vapor deposition. As still another method, the dye may be mixed with another compound and introduced into pores in fabricating a porous material by the sol-get method.

According to the sixth embodiment, the adsorption area of ozone gas to be detected can be increased by using the sensing element containing the dye in the pores of the porous material. Compared to a conventional method, the sensitivity and accumulation capacity can be increased, realizing cumulative use.

Also in the sixth embodiment, the porous material desirably has an average pore diameter of 20 nm or less.

In the sixth embodiment, glycerol is added as an acid gas sorbent. Instead, triethanolamine may be added.

Seventh Embodiment

An ozone gas sensing element according to the seventh embodiment of the present invention will be described.

An ozone gas sensing element fabrication method according to the seventh embodiment will be explained.

As shown in FIG. 1A, a dye solution is prepared by dissolving, in water, indigo carmine disodium salt as a dye (stain), acetic acid as an acid, and glycerol as a hygroscopic compound. The indigo carmine disodium salt concentration is 0.4%, the acetic acid concentration is 1 N, and the glycerol concentration is 10.0%.

As shown in FIG. 1B, a porous material having an average pore diameter of 4 nm is immersed in the dye solution. The porous material is identical to that described in the first embodiment, and is made of Vycor 7930 available from Corning. The porous material has a chip size of 8 (mm)×8 (mm) with a thickness of 1 (mm). The porous material is immersed in the dye solution for 24 hrs to impregnate the pores of the porous material with the dye solution, and then air-dried. The porous material is left dried in a nitrogen gas flow for a day, thereby fabricating a sensing element according to the seventh embodiment.

Figure 13:
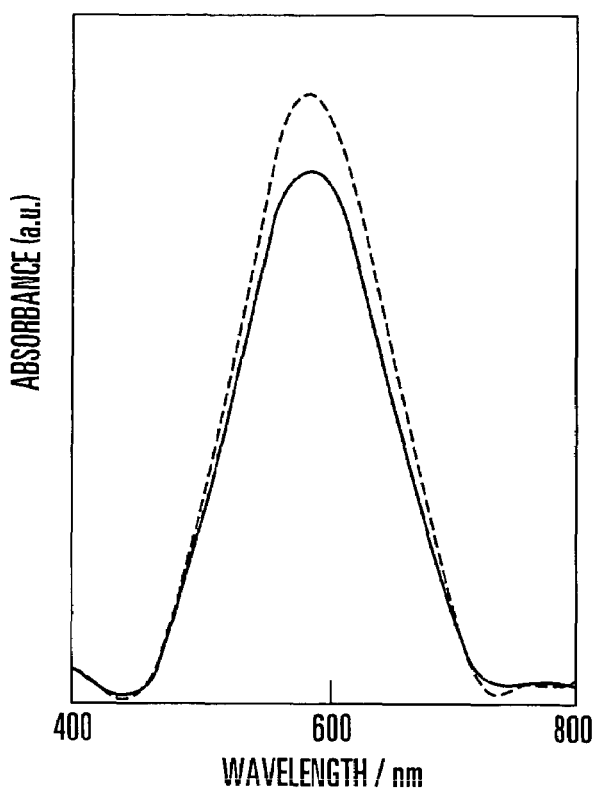
FIG. 13 is a graph showing the results of two absorbance measurements in an ozone gas detection method according to the seventh embodiment of the present invention.

Absorption spectra before and after exposing the sensing element of the seventh embodiment to measurement target air will be described with reference to FIG. 13. In FIG. 13, the broken line represents the absorption spectrum before exposure to measurement target air. The solid line represents the absorption spectrum after exposing the sensing element of the seventh embodiment for 2 hrs to air containing ozone gas at a concentration of 100 ppb.

In the seventh embodiment, as shown in FIG. 13, the solid line exhibits a decrease in absorption around a wavelength of 600 nm. This decrease is about 0.05, and ozone gas can be detected at high-sensitivity ppb level.

In the above-described fabrication method, a comparative sensing element was fabricated except glycerol. The influence of disturbance of a humidity change was investigated using the comparative sensing element. As a result, the comparative sensing element observed disturbance of humidity, but the sensing element of the seventh embodiment hardly observed disturbance.

As described above, the seventh embodiment prepares a sensing element in which an acid, hygroscopic compound, and a dye that irreversibly changes in the absorbance of the visible region upon reaction with ozone gas are deposited in the pores of a transparent porous material. It is estimated that, when the sensing element is exposed to an ozone gas-containing atmosphere, a double bond such as C═C in the dye is broken by ozone gas adsorbed in the pores of the sensing element, and the electron state of the dye molecule changes to change the absorption spectrum of the visible region.

Ozone gas can be detected when the color of the sensing element changes and the first and second transmittances become different.

Since the hygroscopic compound contains water, even addition of moisture upon a humidity change has little influence. Thus, disturbance of humidity can be reduced.

The seventh embodiment has exemplified the use of indigo carmine disodium salt as a dye. An example of a dye is an indigoid stain having an indigo ring (e.g., indigo or indigo carmine tripotassium salt).

Examples of a dye are Orange I, Orange II, Orange G, Methyl Orange, Bismarck Brown, Methyl Yellow, Acid Chrome Violet K, Crocein Orange G, Chromotrope FB, New Coccine, Crystal Scarlet, Alizarin Blue Black R, Plasmocorinth B, Sudan II, Sudan III, Sudan IV, Sudan Red B, Sudan Red 7B, Sunset Yellow FCF, Toluidine Red, Tropaeoline O, Xylidine Ponceau 2R, zincon monosodium salt, Benzopurpurin 4B, Biebrich Scarlet Red, Bordeaux R, Brilliant Crocein MOO, 2-(5-bromo-2-pyridylazo) 5-(diethylamino) phenol, 6'-butoxy-2,6-diamino-3,3'-azodipyridine, Acid Black 24, Acid Blue 29, Acid Blue 92, Acid Blue 113, Acid Blue 120, Acid Orange 8, Acid Orange 51, Acid Orange 63, Acid Orange 74, Acid Red 1, Acid Red 4, Acid Red 8, Acid Red 37, Acid Red 97, Acid Red 114, Acid Red 151, Acid Red 183, Acid Violet 7, Acid Yellow 17, Acid Yellow 25, Acid Yellow 29, Acid Yellow 34, Acid Yellow 42, Acid Yellow 76, Acid Yellow 99, Alizarin Yellow GG, Allura Red AC, Amaranth, Calcion, Chicago Sky Blue 6B, Chromotrope 2B, Chromotrope 2R, chrysoidin, Congo Red, Direct Blue 71, Direct Red 23, Direct Red 75, Direct Red 80, Direct Red 81, Direct Violet 51, Direct Yellow 50, Direct Yellow 62, Disperse Red 1, Disperse Red 19, Disperse Yellow 3, Eriochrome Blue Black B, Eriochrome Black T, Evans Blue, Fat Brown RR, Metanil Yellow, Naphthol Blue Black, Nitrazine Yellow, Nitro Red, Nitrosulfonazo III, Solvent Red 26, and Oil Red O. An example of a dye is a dye which is an aromatic compound (e.g., benzene, naphthalene, or anthracene) and has a diazo group. By using these dyes, ozone can be specifically detected even in the presence of another gas.

An example of a dye is a diazo dye which contains a dye as an aromatic compound (e.g., benzene, naphthalene, or anthracene) having a diazo group and has a hydroxyl group, a sulfurous acid group, or primary to tertiary amino groups. By using these dyes, ozone can be specifically detected even in the presence of another gas. In addition, the stability of the dye can be obtained to more stably detect ozone.

In the seventh embodiment, the dye solution 101 is prepared by adding acetic acid as an acid. Any one of hydrochloric acid, sulfuric acid, and phosphoric acid may be used.

In the seventh embodiment, the dye solution 101 is prepared by adding glycerol as a hygroscopic compound. Alternatively, ethylene glycol may be used.

As a method of introducing a dye into the pores of a porous material, the porous material is impregnated with the dye by using the dye solution, and the dye is introduced into pores and dried. As another method, the dye may be introduced into pores by vapor deposition. As still another method, the dye may be mixed with another compound and introduced into pores in fabricating a porous material by the sol-get method.

According to the seventh embodiment, the adsorption area of ozone gas to be detected can be increased by using the sensing element containing the dye in the pores of the porous material. Compared to a conventional method, the sensitivity and accumulation capacity can be increased, realizing cumulative use.

Also in the seventh embodiment, the porous material preferably has an average pore diameter of 20 nm or less.

Eighth Embodiment

An ozone gas sensing element according to the eighth embodiment of the present invention will be described.

An ozone gas sensing element fabrication method according to the eighth embodiment will be explained.

As shown in FIG. 1A, a dye solution is prepared by dissolving, in water, indigo carmine disodium salt as a dye (stain), and phosphoric acid and sodiumdihydrogenphosphate dihydrate as a buffer. The indigo carmine disodium salt concentration is 0.4%, the phosphoric acid concentration is 50 mmol, and the sodiumdihydrogenphosphate dehydrate concentration is 50 mmol.

As shown in FIG. 1B, a porous material having an average pore diameter of 4 nm is immersed in the dye solution. The porous material is identical to that described in the first embodiment, and is made of Vycor 7930 available from Corning. The porous material has a chip size of 8 (mm)×8 (mm) with a thickness of 1 (mm). The porous material is immersed in the dye solution for 24 hrs to impregnate the pores of the porous material with the dye solution, and then air-dried. The porous material is left dried in a nitrogen gas flow for a day, thereby fabricating a sensing element according to the eighth embodiment.

Figure 14:
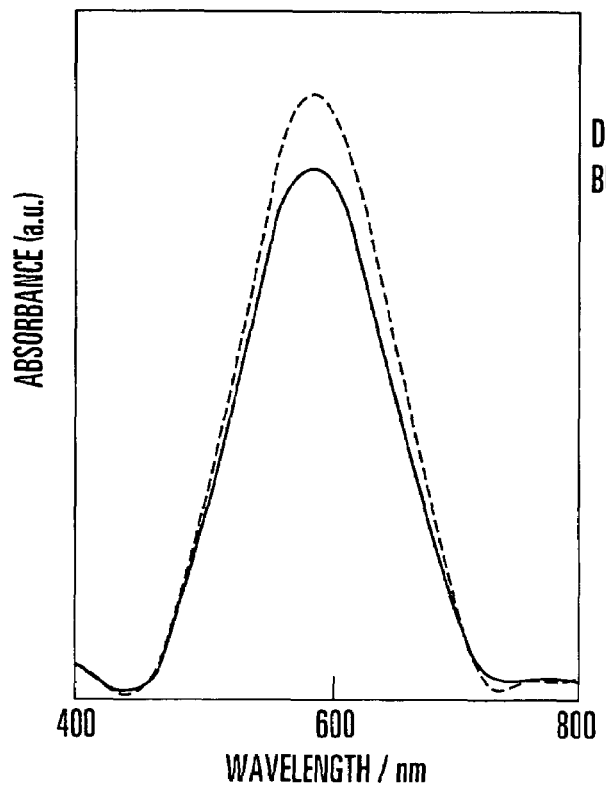
FIG. 14 is a graph showing the results of two absorbance measurements in an ozone gas detection method according to the eighth embodiment of the present invention.

Absorption spectra before and after exposing the sensing element of the eighth embodiment to measurement target air will be described with reference to FIG. 14. In FIG. 14, the broken line represents the absorption spectrum before exposure to measurement target air. The solid line represents the absorption spectrum after exposing the sensing element of the eighth embodiment for 2 hrs to air containing ozone gas at a concentration of 100 ppb.

In the eighth embodiment, as shown in FIG. 14, the solid line exhibits a decrease in absorption around a wavelength of 600 nm. This decrease is about 0.05, and ozone gas can be detected at high-sensitivity ppb level.

In the above-described fabrication method, a comparative sensing element was fabricated except a buffer. The influence of disturbance of a humidity change was investigated using the comparative sensing element. As a result, the comparative sensing element observed disturbance of humidity, but the sensing element of the eighth embodiment hardly observed disturbance.

As described above, the eighth embodiment prepares a sensing element in which a mixture of a buffer and a dye that changes in the absorbance of the visible region upon reaction with ozone gas is deposited in the pores of a transparent porous material. It is estimated that, when the sensing element is exposed to an ozone gas-containing atmosphere, a carbon-carbon double bond in an indigo ring contained in the dye is broken by ozone gas deposited in the pores of the sensing element, and the electron state of the dye molecule changes to change the absorption spectrum of the visible region. Hence, ozone gas can be detected when the color of the sensing element changes and the first and second transmittances become different.

By adding the buffer, the hydrogen ion concentration can be kept constant even upon addition of moisture by a humidity change, and disturbance of humidity can be reduced.

The seventh embodiment has exemplified the use of indigo carmine disodium salt as a dye. An example of a dye is an indigoid stain having an indigo ring (e.g., indigo or indigo carmine tripotassium salt).

Examples of a dye are Orange I, Orange II, Orange G, Methyl Orange, Bismarck Brown, Methyl Yellow, Acid Chrome Violet K, Crocein Orange G, Chromotrope FB, New Coccine, Crystal Scarlet, Alizarin Blue Black R, Plasmocorinth B, Sudan II, Sudan III, Sudan IV, Sudan Red B, Sudan Red 7B, Sunset Yellow FCF, Toluidine Red, Tropaeoline O, Xylidine Ponceau 2R, zincon monosodium salt, Benzopurpurin 4B, Biebrich Scarlet Red, Bordeaux R, Brilliant Crocein MOO, 2-(5-bromo-2-pyridylazo) 5-(diethylamino) phenol, 6'-butoxy-2,6-diamino-3,3'-azodipyridine, Acid Black 24, Acid Blue 29, Acid Blue 92, Acid Blue 113, Acid Blue 120, Acid Orange 8, Acid Orange 51, Acid Orange 63, Acid Orange 74, Acid Red 1, Acid Red 4, Acid Red 8, Acid Red 37, Acid Red 97, Acid Red 114, Acid Red 151, Acid Red 183, Acid Violet 7, Acid Yellow 17, Acid Yellow 25, Acid Yellow 29, Acid Yellow 34, Acid Yellow 42, Acid Yellow 76, Acid Yellow 99, Alizarin Yellow GG, Allura Red AC, Amaranth, Calcion, Chicago Sky Blue 6B, Chromotrope 2B, Chromotrope 2R, chrysoidin, Congo Red, Direct Blue 71, Direct Red 23, Direct Red 75, Direct Red 80, Direct Red 81, Direct Violet 51, Direct Yellow 50, Direct Yellow 62, Disperse Red 1, Disperse Red 19, Disperse Yellow 3, Eriochrome Blue Black B, Eriochrome Black T, Evans Blue, Fat Brown RR, Metanil Yellow, Naphthol Blue Black, Nitrazine Yellow, Nitro Red, Nitrosulfonazo III, Solvent Red 26, and Oil Red O. An example of a dye is a dye which is an aromatic compound (e.g., benzene, naphthalene, or anthracene) and has a diazo group. By using these dyes, ozone can be specifically detected even in the presence of another gas.

An example of a dye is a diazo dye which contains a dye as an aromatic compound (e.g., benzene, naphthalene, or anthracene) having a diazo group and has a hydroxyl group, a sulfurous acid group, or primary to tertiary amino groups. By using these dyes, ozone can be specifically detected even in the presence of another gas. In addition, the stability of the dye can be obtained to more stably detect ozone.

As a method of introducing a dye into the pores of a porous material, the porous material is impregnated with the dye by using the dye solution, and the dye is introduced into pores and dried. As another method, the dye may be introduced into pores by vapor deposition. As still another method, the dye may be mixed with another compound and introduced into pores in fabricating a porous material by the sol-get method.

According to the eighth embodiment, the adsorption area of ozone gas to be detected can be increased by using the sensing element containing the dye in the pores of the porous material. Compared to a conventional method, the sensitivity and accumulation capacity can be increased, realizing cumulative use.

Also in the eighth embodiment, the porous material preferably has an average pore diameter of 20 nm or less.

The first to eighth embodiments have described a plate-like sensing element. The sensing element is not limited to this, and may be shaped into a fiber.

In the above-described embodiments, the dye (stain) is deposited in the pores of a porous material. The present invention is not limited to the porous material, and can employ any material as far as dye states before and after reaction with ozone can be measured.

Ninth Embodiment

The ninth embodiment of the present invention will be described.

Figure 15:
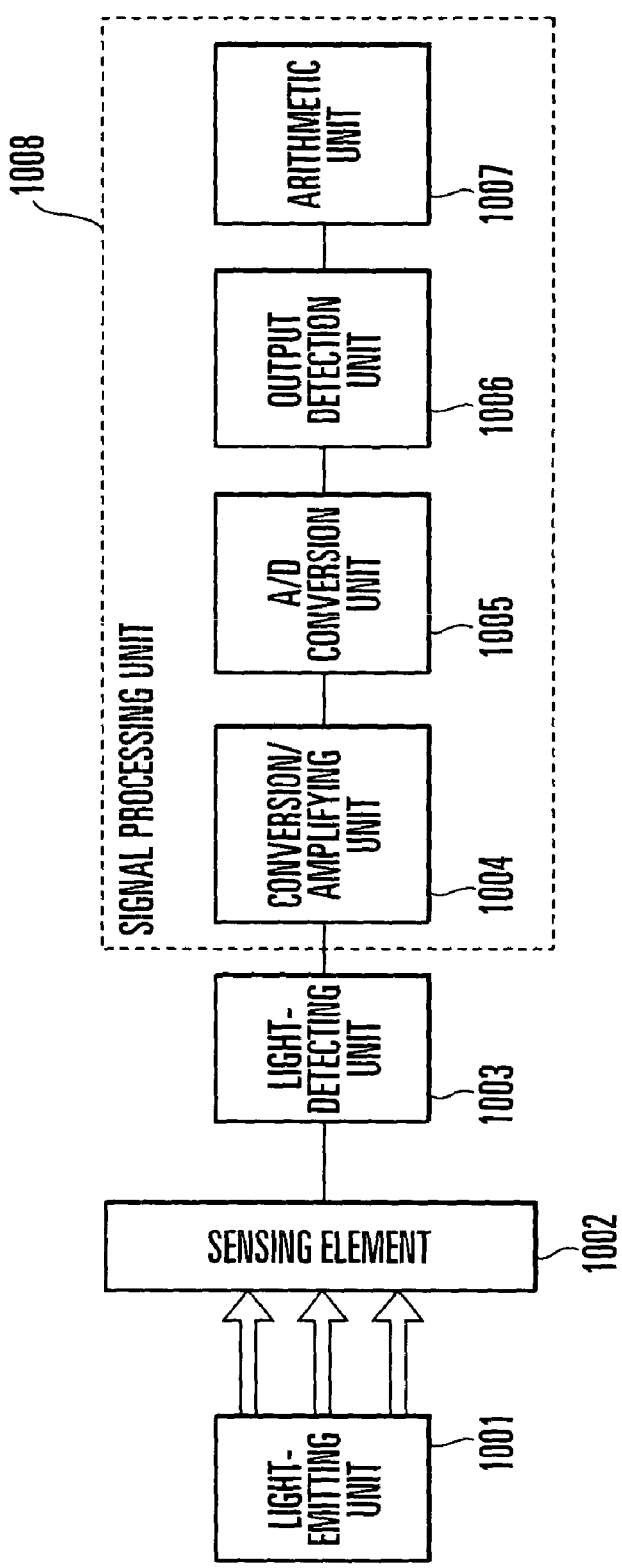
FIG. 15 is a block diagram showing the schematic arrangement of an ozone gas detection apparatus according to an embodiment of the present invention.

As shown in FIG. 15, an ozone gas detection apparatus (measurement apparatus) according to the ninth embodiment comprises a light-emitting unit 1001 which emits light having a predetermined wavelength, a sensing element 1002 which senses light emitted by the light-emitting unit 1001, a light-detecting unit 1003 which is connected to the sensing element 1002 and receives light having passed through the sensing element 1002, and a signal processing unit 1008 which is connected to the light-detecting unit 1003.

The signal processing unit 1008 comprises a conversion/amplifying unit 1004 which is connected to the light-detecting unit 1003, an A/D conversion unit 1005 which is connected to the conversion/amplifying unit 1004, an output detection unit 1006 which is connected to the A/D conversion unit 1005, and an arithmetic unit 1007 which is connected to the output detection unit 1006.

For example, the sensing element 1002 is irradiated with light emitted by the light-emitting unit 1001 which is constituted by an LED for emitting light having a predetermined wavelength. Light having passed through the sensing element 1002 is received by the light-detecting unit 1003. The light-detecting unit 1003 photoelectrically converts received light and outputs a signal current. The conversion/amplifying unit 1004 amplifies the output signal current, and converts the current into a voltage. The A/D conversion unit 1005 converts the voltage signal into a digital signal. The output detection unit 1006 outputs the digital signal as a detection result. The arithmetic unit 1007 calculates an ozone gas amount on the basis of the signal output from the output detection unit 1006 and the light absorption characteristic, obtained in advance, of the sensing element which contains a dye 303 before reaction with ozone gas 304.

The sensing element 1002 is a sensing element according to any one of the first to eighth embodiments described above. The light-emitting unit 1001 can adopt a blue LED having an emission wavelength of, e.g., 470 nm.

For example, ozone gas was detected in a dry air atmosphere and air at an ozone concentration of 50 ppb to 500 ppb by using a detection apparatus (measurement apparatus) having a sensing element according to the first embodiment.

It is estimated that, when ozone gas enters the pores of the sensing element and adsorbed, a double bond such as N=N or C=C in the dye is broken, and the electron state of the dye molecule changes to change the color of the sensing element. As a result, the absorption spectrum of the visible range changes. Light emitted by the light-emitting unit 1001 enters the light-receiving unit 1003 via the sensing element 1002, and a change in the color of the sensing element 1002 can be measured as a change in electrical signal output from the light-receiving unit 1003 by an electric instrument which performs signal processing.

Consequently, as described above, an output different from the initial state in which the sensing element is not exposed to ozone gas can be obtained.

According to the ninth embodiment, the ozone gas detection apparatus (measurement apparatus) can be easily constituted.

As described above, the ozone gas sensing element according to the present invention comprises a porous material, and a dye which is deposited in the pores of the porous material and changes in the light absorption characteristic of the visible region upon reaction with ozone gas. With this arrangement, when ozone gas enters the pores of the ozone gas sensing element and is adsorbed, the dye is decomposed to fade the color of the ozone gas sensing element. By checking a color change, ozone gas can be detected. Ozone gas can be detected more easily at higher precision than a conventional method.

A dye which is an aromatic compound (e.g., benzene, naphthalene, or anthracene) and has a diazo group can specifically detect ozone even in the presence of another gas.

A dye which is an aromatic compound (e.g., benzene, naphthalene, or anthracene) and has a hydroxyl group, a sulfurous acid group, or primary to tertiary amino groups in addition to a diazo group can specifically detect ozone even in the presence of another gas. Further, the stability of the dye can be obtained to more stably detect ozone.

When a triphenylmethane stain dye is used as a dye, ozone can be specifically detected even in the presence of another gas.

When a fuchsonimine-containing dye is used as a dye, ozone can be specifically detected even in the presence of another gas.

When an indigoid stain having an indigo ring is used as a dye, ozone can be specifically detected even in the presence of another gas.

Since a triphenylmethane stain dye or fuchsonimine dye and alkali are deposited in the pores of the porous material, the absorbance can be stabilized even in nitrogen without any change.

Since a dye and acid gas sorbent are deposited in the pores of the porous material, ozone can be detected without disturbance by $NO_2$. As the acid gas sorbent, either of glycerol and triethanolamine can be employed. The average pore diameter of the porous material is set to 20 nm or less at which the dye can enter pores. In measurement of the absorption spectrum in the UV visible wavelength region (wavelength of 200 nm to 2,000 nm), a larger quantity of light can be transmitted in the visible light region (350 nm to 800 nm).

A diazo dye or indigoid dye and an acid are deposited in the pores of the porous material. With this arrangement, when ozone gas enters the pores of the ozone gas sensing element and is adsorbed, the dye is decomposed to fade the color of the ozone gas sensing element. By checking a color change, ozone gas can be detected. Ozone gas can be detected more easily at higher precision than a conventional method.

In the ozone gas sensing element, an acid is selected as one of hydrochloric acid, acetic acid, sulfuric acid, and phosphoric acid. Many dye components can be mixed in the porous material.

In the ozone gas sensing element, glycerol is deposited together with the dye and acid in the pores of the porous material, thus preventing disturbance of $NO_2$.

In the ozone gas sensing element, the average pore diameter of the porous material is set to less than 20 nm at which the dye can enter pores. In measurement of the absorption spectrum in the UV visible wavelength region (wavelength of 200 nm to 2,000 nm), a larger quantity of light can be transmitted in the visible light region (350 nm to 800 nm).

A diazo dye or indigoid dye, an acid, and a hygroscopic compound are deposited in the pores of the porous material. With this arrangement, when ozone gas enters the pores of the ozone gas sensing element and is adsorbed, the dye is decomposed to fade the color of the ozone gas sensing element. By checking a color change, ozone gas can be detected. Ozone gas can be detected more easily at higher precision than a conventional method.

In the ozone gas sensing element, an acid is selected as one of hydrochloric acid, acetic acid, sulfuric acid, and phosphoric acid. Many dye components can be mixed in the porous material.

In the ozone gas sensing element, examples of a hygroscopic component are glycerol and ethylene glycol. A large amount of water can be held in the porous material to reduce the influence of humidity.

In the ozone gas sensing element, the average pore diameter of the porous material is set to less than 20 nm at which the dye can enter pores. In measurement of the absorption spectrum in the UV visible wavelength region (wavelength of 200 nm to 2,000 nm), a larger quantity of light can be transmitted in the visible light region (350 nm to 800 nm).

A diazo dye or indigoid dye and a buffer are deposited in the pores of the porous material. With this arrangement, when ozone gas enters the pores of the ozone gas sensing element and is adsorbed, the dye is decomposed to fade the color of the ozone gas sensing element. By checking a color change, ozone gas can be detected. Ozone gas can be detected more easily at higher precision than a conventional method.

Since the buffer is introduced in the ozone gas sensing element, the hydrogen ion concentration in the porous material can be maintained almost free from the influence of humidity.

In the ozone gas sensing element, the average pore diameter of the porous material is set to less than 20 nm at which the dye can enter pores. In measurement of the absorption spectrum in the UV visible wavelength region (wavelength of 200 nm to 2,000 nm), a larger quantity of light can be transmitted in the visible light region (350 nm to 800 nm).

The adsorption area of ozone gas to be detected can be increased by using the sensing element containing a dye in the pores of the porous material. Compared to a conventional method, the sensitivity and accumulation capacity can be increased, realizing cumulative use.

The ozone gas detection apparatus (measurement apparatus) of the present invention comprises a light-emitting unit, light-detecting unit, sensing element, and signal processing unit. The light-emitting unit emits light having a predetermined wavelength. The sensing element is interposed between the light-emitting unit and the light-detecting unit, and comprises a porous material, and a dye which is deposited in the pores of the porous material and changes in the light absorption characteristic of the visible region upon reaction with ozone gas. The light-detecting unit comprises a light-receiving surface which is arranged to face the light-emitting unit. The light-detecting unit receives, via the sensing element, light emitted by the light-emitting unit, and outputs a signal corresponding to a light quantity received by the light-receiving surface. The signal processing unit calculates an ozone gas amount on the basis of the signal output from the light-detecting unit and the light absorption characteristic, obtained in advance, of the sensing element which contains a dye before reaction with ozone gas.

With this arrangement, when ozone gas enters the pores of the sensing element and is adsorbed, the dye is decomposed to fade the color of the sensing element. Light emitted by the light-emitting unit enters the light-detecting unit via the sensing element. A change in the color of the sensing element is measured as a change in electrical signal output from the light-detecting unit by an electric instrument.

The ozone gas detection apparatus (measurement apparatus) can be arranged in a measurement target atmosphere to detect ozone gas at high precision. Compared to a conventional method, ozone gas can be detected more easily at higher precision.

For example, the light-emitting unit is constituted by a light-emitting diode, and the light-detecting unit is constituted by a phototransistor. Further, the detection apparatus comprises a battery which supplies power to the light-emitting diode and phototransistor, a switch which supplies or stops power from the battery to the light-emitting diode and phototransistor, and a voltmeter serving as an electric instrument which is connected between the phototransistor and the battery the detection apparatus also comprises a terminal strip having terminals for connecting the light-emitting diode, phototransistor, battery, switch, and voltmeter, and a board on which the light-emitting diode, phototransistor, battery, switch, voltmeter, and terminal strip are arranged.

Accordingly, a high-precision ozone gas detection apparatus (measurement apparatus) can be constituted within a small area. A commercially available battery can be used as a power supply, and ozone gas can be more easily detected.

An ozone gas detection method (measurement method) according to the present invention comprises the step of preparing a sensing element in which a dye that changes in the light absorption characteristic of the visible region upon reaction with ozone gas is deposited in the pores of a porous material, the step of exposing the sensing element to a measurement environment for a predetermined time, and the step of measuring an ozone gas amount in a measurement target gas on the basis of a change in dye before and after exposing the sensing element to the measurement environment for a predetermined time. More specifically, the ozone gas detection method (measurement method) comprises the first step of measuring the light transmittance of a sensing element according to the present invention to obtain the first transmittance, the second step of exposing the sensing element to a measurement target gas for a predetermined time, the third step of measuring the light transmittance of the sensing element to obtain the second transmittance, and the fourth step of detecting ozone in the measurement target from the difference between the first and second transmittances.

With these steps, when the sensing element is exposed to an ozone gas-containing atmosphere, the dye adsorbed in the pores of the sensing element is decomposed. The color of the sensing element changes to generate a difference between the first and second transmittances. Thus, ozone gas can be detected. Only a change in the color of the sensing element is observed after the sensing element is exposed to a measurement target atmosphere. Ozone gas can be detected more easily at higher precision than a conventional method.

What is claimed is:

1. An ozone gas sensing element comprising:
   a transparent porous material comprising a water film formed in a pore of the porous material; and
   a dye which is deposited in the pore of said porous material and changes in a light absorption characteristic of a visible region upon reaction with ozone gas.

2. An element according to claim 1, wherein at least some pores in said porous material are coupled to pores on a surface of said porous material.

3. An element according to claim 1, wherein a pore in said porous material has such a pore diameter as to attain a predetermined transmittance in the visible light region.

4. An element according to claim 3, wherein the pore diameter is not more than 20 nm at which the dye can enter the pore.

5. An ozone gas sensing element comprising:
   a transparent porous material; and
   a dye which is deposited in a pore of said porous material and changes in a light absorption characteristic of a visible region upon reaction with ozone gas, wherein the dye comprises an aromatic compound having a diazo group.

6. An element according to claim 5, wherein the aromatic compound comprises one material selected from the group consisting of benzene, naphthalene, and anthracene.

7. An element according to claim 5, wherein the dye comprises a compound having any one of a hydroxyl group, a sulfurous acid group, and primary to tertiary amino groups.

8. An element according to claim 1, wherein the dye comprises a triphenylmethane stain.

9. An ozone gas sensing element comprising:
   a transparent porous material; and
   a dye which is deposited in a pore of said porous material and changes in a light absorption characteristic of a visible region upon reaction with ozone gas, wherein the dye contains fuchsonimine.

10. An element according to claim 1, wherein the dye contains indigo carmine.

11. An element according to claim 9, wherein said sensing element further comprises a material having an alkali characteristic in addition to the dye.

12. An ozone gas sensing element comprising:
    a transparent porous material; and
    a dye which is deposited in a pore of said porous material and changes in a light absorption characteristic of a visible region upon reaction with ozone gas, wherein said sensing element further comprises an acid gas sorbent in addition to the dye.

13. An element according to claim 12, wherein the acid gas sorbent comprises one material selected from the group consisting of glycerol and triethanolamine.

14. An element according to claim 10, wherein said sensing element further comprises an acid in addition to the dye.

15. An element according to claim 14, wherein the acid comprises one acid selected from the group consisting of hydrochloric acid, acetic acid, sulfuric acid, and phosphoric acid.

16. An element according to claim 14, wherein said sensing element further comprises a hygroscopic compound in addition to the dye and the acid.

17. An element according to claim 16, wherein the hygroscopic compound comprises one material selected from the group consisting of glycerol and ethylene glycol.

18. An element according to claim 10, wherein said sensing element further comprises a buffer in addition to the dye.

19. An element according to claim 18, wherein the buffer comprises phosphoric acid and sodiumdihydrogenphosphate dehydrate.

20. An element according to claim 8, wherein said sensing element further comprises a material having an alkali characteristic in addition to the dye.

21. An element according to claim 5, wherein said sensing element further comprises an acid in addition to the dye.

22. An element according to claim 5, wherein said sensing element further comprises a buffer in addition to the dye.

* * * * *